(12) United States Patent
Takenaka

(10) Patent No.: US 9,451,184 B2
(45) Date of Patent: Sep. 20, 2016

(54) PHOTO CONDUCTIVE ANTENNA, CAMERA, IMAGING APPARATUS, AND MEASUREMENT APPARATUS

(71) Applicant: SEIKO EPSON CORPORATION, Tokyo (JP)

(72) Inventor: Satoshi Takenaka, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 382 days.

(21) Appl. No.: 14/192,592

(22) Filed: Feb. 27, 2014

(65) Prior Publication Data

US 2014/0240510 A1    Aug. 28, 2014

(30) Foreign Application Priority Data

Feb. 27, 2013  (JP) ................. 2013-036770

(51) Int. Cl.
*G01N 21/35*      (2014.01)
*H04N 5/33*       (2006.01)
*G01N 21/3581*    (2014.01)

(52) U.S. Cl.
CPC ............ *H04N 5/33* (2013.01); *G01N 21/3581* (2013.01)

(58) Field of Classification Search
CPC ................................................. G01N 21/3581
See application file for complete search history.

(56) References Cited

U.S. PATENT DOCUMENTS

| | | | |
|---|---|---|---|
| 6,759,137 B1 | 7/2004 | Furuya et al. | |
| 7,659,137 B2 | 2/2010 | Kasai et al. | |
| 8,093,560 B2 | 1/2012 | Kuroyanagi et al. | |
| 2001/0029436 A1* | 10/2001 | Fukasawa | G01N 21/3581 702/117 |
| 2010/0052083 A1* | 3/2010 | Kasai | H01L 31/0352 257/431 |
| 2010/0310976 A1* | 12/2010 | Kajiki | H01L 31/09 430/56 |
| 2011/0127431 A1 | 6/2011 | Paek | |

FOREIGN PATENT DOCUMENTS

| | | |
|---|---|---|
| JP | 2000-049403 A | 2/2000 |
| JP | 2003-015175 A | 1/2003 |
| JP | 2005-322733 A | 11/2005 |
| JP | 2007-278740 A | 10/2007 |
| JP | 2009-124437 A | 6/2009 |
| JP | 2010-118365 A | 5/2010 |
| JP | 2010-187007 A | 8/2010 |
| JP | 2011-119642 A | 6/2011 |

OTHER PUBLICATIONS

"Laser Studies" academic journal of the Laser Society of Japan, vol. 26, No. 7, Jul. 1998.

* cited by examiner

*Primary Examiner* — Casey Bryant
(74) *Attorney, Agent, or Firm* — Maschoff Brennan

(57) ABSTRACT

A photo conductive antenna irradiated with light pulse and generating terahertz wave includes a first layer formed by a semi-insulating substrate, a second layer located on the first layer and formed using a material having lower carrier mobility than carrier mobility of the semi-insulating substrate, a first electrode and a second electrode located on the second layer and applying a voltage to the first layer, a first region in which the second layer is formed on the first layer, and a second region in which the second layer is formed on the first layer, wherein the second region is located between the first electrode and the second electrode in a plan view, and the light pulse is applied to the second region.

19 Claims, 14 Drawing Sheets

PHOTO CONDUCTIVE ANTENNA, CAMERA, IMAGING APPARATUS, AND MEASUREMENT APPARATUS

BACKGROUND

1. Technical Field

The present invention relates to a photo conductive antenna, a camera, an imaging apparatus, and a measurement apparatus.

2. Related Art

Recently, terahertz wave as electromagnetic wave having frequencies from 100 GHz to 30 THz has attracted attention. The terahertz wave may be used for imaging, various kinds of measurement including spectroscopic measurement, nondestructive test, etc., for example.

A terahertz wave generator that generates the terahertz wave has a light pulse generation unit that generates light pulse with a pulse width of about subpicoseconds (several hundreds of femtoseconds) and a photo conductive antenna (PCA) that generates terahertz wave by application of the light pulse generated by the light pulse generation unit, for example.

For example, Patent Document 1 (JP-A-2009-124437) has disclosed a photo conductive antenna including a semi-insulating GaAs substrate, a GaAs (LT-GaAs) layer formed by low-temperature MBE (molecular beam epitaxy) on the semi-insulating GaAs substrate, and a pair of electrodes formed on the LT-GaAs layer. Further, Patent Document 1 has disclosed that free carriers excited in the LT-GaAs layer are accelerated by an electric field of a bias voltage, a current flows, and terahertz wave is generated due to change of the current.

It is desirable that the strength of the terahertz wave generated in the photo conductive antenna is larger, and thereby, for example, an imaging apparatus and a measurement apparatus with higher detection sensitivity may be realized.

It is known that the strength of the terahertz wave generated in the photo conductive antenna depends on electron mobility (carrier mobility) of a receiving part of pulsed light in the photo conductive antenna. That is, the larger the carrier mobility of the receiving part, the higher the strength of the terahertz wave generated in the photo conductive antenna.

In the photo conductive antenna of Patent Document 1, the carrier mobility of the LT-GaAs layer is smaller, and it may be impossible to generate the terahertz wave with the higher strength or realize an imaging apparatus and a measurement apparatus with the higher detection sensitivity.

SUMMARY

An advantage of some aspects of the invention is to provide a photo conductive antenna that may make carrier mobility higher and generate terahertz wave with the higher strength than those in related art. Another advantage of some aspects of the invention is to provide a camera, an imaging apparatus, and a measurement apparatus including the photo conductive antenna.

An aspect of the invention is directed to a photo conductive antenna irradiated with light pulse and generating terahertz wave, and including a first layer formed by a semi-insulating substrate, a second layer located on the first layer and formed using a material having lower carrier mobility than carrier mobility of the semi-insulating substrate, a first electrode and a second electrode located on the second layer and applying a voltage to the first layer, a first region in which the second layer is formed on the first layer, and a second region in which the second layer is formed on the first layer, wherein the second region is located between the first electrode and the second electrode in a plan view from a stacking direction of the first layer and the second layer, and the light pulse is applied to the second region.

According to the photo conductive antenna, the light pulse is applied to the first layer formed by the semi-insulating substrate. The carrier mobility of the semi-insulating substrate is larger than the carrier mobility of the material forming the second layer. Accordingly, the photo conductive antenna may improve the carrier mobility and generate terahertz wave with the higher strength.

Further, in the photo conductive antenna, the second layer is located between the first layer and the first electrode and the second electrode, and the second layer is formed by the material having the smaller carrier mobility than the carrier mobility of the semi-insulating substrate forming the first layer. Accordingly, the probability of the carriers (electrons) generated within the first layer reaching the first electrode and the second electrode may be made lower. That is, with the second layer, the probability of extinction of the carriers generated within the first layer before reaching the first electrode and the second electrode may be made higher. As a result, the photo conductive antenna may have the higher withstand voltage.

The photo conductive antenna of the aspect of the invention may be configured such that the first electrode has a first projecting part that projects from the first electrode toward the second electrode side in the plan view, the second electrode has a second projecting part that projects from the second electrode toward the first electrode side in the plan view, and the first region and the second region are provided in a region between the first projecting part and the second projecting part in the plan view.

According to the photo conductive antenna with this configuration, the terahertz wave with the higher strength may be generated.

The photo conductive antenna of the aspect of the invention may be configured such that the first electrode and the second electrode apply a direct-current voltage to the first layer, the first electrode is a positive electrode, the second electrode is a negative electrode, and a distance between the second region and the first projecting part is larger than a distance between the second region and the second projecting part in the plan view.

According to the photo conductive antenna with this configuration, the probability of extinction of the electrons generated within the first layer before reaching the first electrode (positive electrode) may be made higher. As a result, the photo conductive antenna may have the higher withstand voltage.

The photo conductive antenna of the aspect of the invention may be configured such that the first electrode and the second electrode apply an alternating-current voltage to the first layer, and a distance between the second region and the first projecting part and a distance between the second region and the second projecting part are equal to each other in the plan view.

According to the photo conductive antenna with this configuration, the probability of extinction of the electrons generated within the first layer before reaching the positive electrode may be made higher. As a result, the photo conductive antenna may have the higher withstand voltage.

The photo conductive antenna of the aspect of the invention may be configured such that the first electrode has a first projecting part that projects from the first electrode toward the second electrode side in the plan view, the second electrode has a second projecting part that projects from the second electrode toward the first electrode side in the plan view, and a region between the first projecting part and the second projecting part in the plan view is the second region.

The photo conductive antenna of the aspect of the invention may be configured such that a covering layer provided on a surface of the first layer is provided.

According to the photo conductive antenna with this configuration, generation of leak current may be suppressed by the covering layer, and the higher withstand voltage may be provided.

The photo conductive antenna of the aspect of the invention may be configured such that a recessed part is formed on a surface of the second layer, and the first electrode and the second electrode are provided in the recessed part.

According to the photo conductive antenna with this configuration, the voltage applied to the first layer by the first electrode and the second electrode may be made higher. Accordingly, the photo conductive antenna may generate terahertz wave with the higher strength.

Another aspect of the invention is directed to a terahertz wave generator including a light pulse generation unit that generates the light pulse, and the photo conductive antenna irradiated with the light pulse and generating the terahertz wave according to the aspect of the invention.

According to the terahertz wave generator, the photo conductive antenna according to the aspect of the invention is provided, and thereby, terahertz wave with the higher strength may be generated.

Still another aspect of the invention is directed to a camera including a light pulse generation unit that generates the light pulse, the photo conductive antenna irradiated with light pulse and generating terahertz wave according to the aspect of the invention, a terahertz wave detection unit that detects the terahertz wave output from the photo conductive antenna and transmitted through an object or reflected by the object, and a memory unit that stores a detection result of the terahertz wave detection unit.

According to the camera, the photo conductive antenna according to the aspect of the invention is provided, and thereby, the higher detection sensitivity may be provided.

Yet another aspect of the invention is directed to an imaging apparatus including a light pulse generation unit that generates the light pulse, the photo conductive antenna irradiated with light pulse and generating terahertz wave according to the aspect of the invention, a terahertz wave detection unit that detects the terahertz wave output from the photo conductive antenna and transmitted through an object or reflected by the object, and an image formation unit that generates an image of the object based on a detection result of the terahertz wave detection unit.

According to the imaging apparatus, the photo conductive antenna according to the aspect of the invention is provided, and thereby, the higher detection sensitivity may be provided.

Still yet another aspect of the invention is directed to a measurement apparatus including a light pulse generation unit that generates the light pulse, the photo conductive antenna irradiated with light pulse and generating terahertz wave according to the aspect of the invention, a terahertz wave detection unit that detects the terahertz wave output from the photo conductive antenna and transmitted through an object or reflected by the object, and a measurement unit that measures the object based on a detection result of the terahertz wave detection unit.

According to the measurement apparatus, the photo conductive antenna according to the aspect of the invention is provided, and thereby, the higher detection sensitivity may be provided.

BRIEF DESCRIPTION OF THE DRAWINGS

The invention will be described with reference to the accompanying drawings, wherein like numbers reference like elements.

DESCRIPTION OF EXEMPLARY EMBODIMENTS

As below, embodiments of the invention will be explained in detail with reference to the drawings. Note that the embodiments to be explained do not unduly limit the invention described in the appended claims. Further, not all of the configurations to be explained are essential component elements of the invention.

1. First Embodiment

1.1. Photo Conductive Antenna

Figure 1:
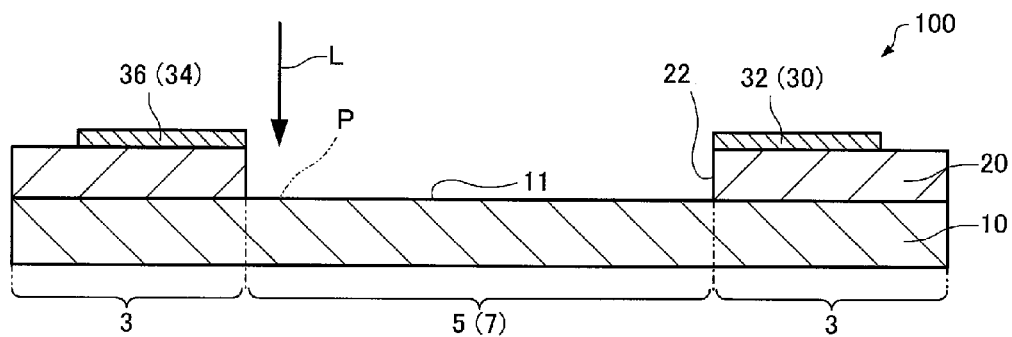
FIG. 1 is a sectional view schematically showing a photo conductive antenna according to the first embodiment.
Figure 2:
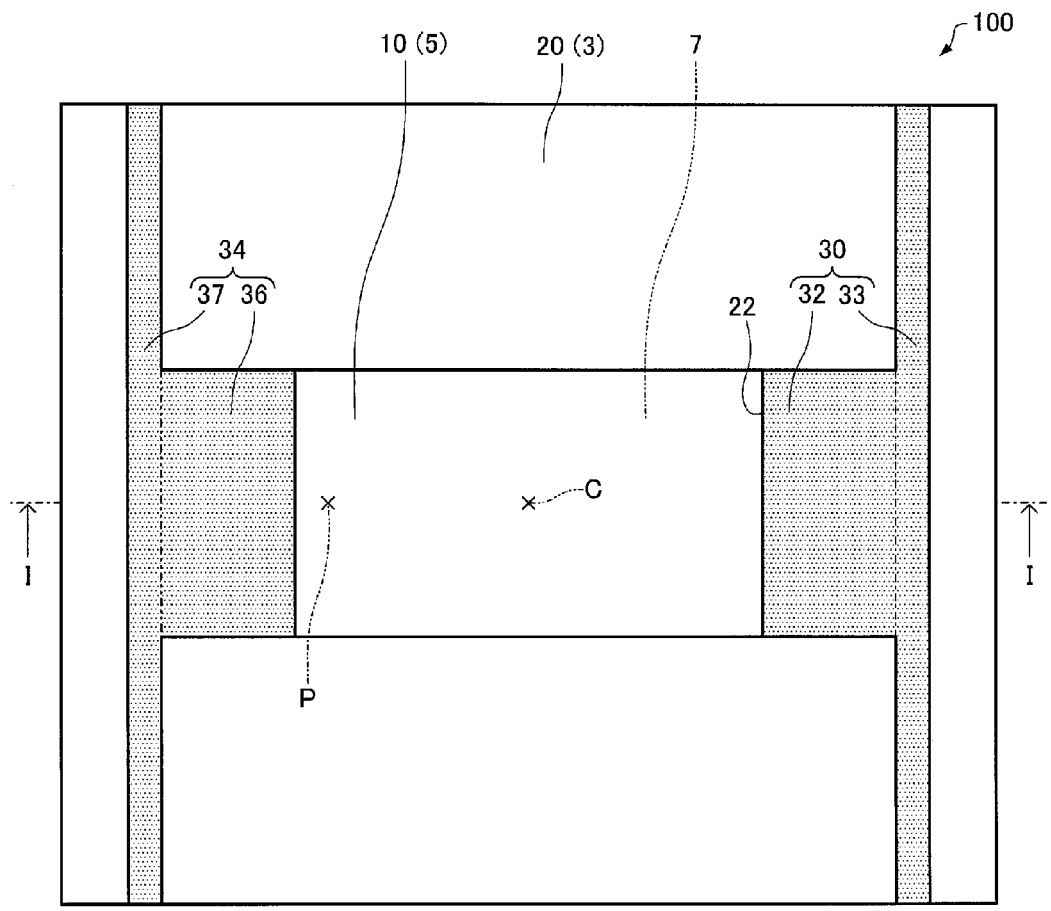
FIG. 2 is a plan view schematically showing the photo conductive antenna according to the first embodiment.

First, a photo conductive antenna according to the first embodiment will be explained with reference to the drawings. FIG. 1 is a sectional view schematically showing a photo conductive antenna 100 according to the first embodiment. FIG. 2 is a plan view schematically showing the photo conductive antenna 100 according to the first embodiment. FIG. 1 is the sectional view along I-I line of FIG. 2.

The photo conductive antenna 100 includes a first layer 10, a second layer 20, a first electrode 30, and a second electrode 34 as shown in FIGS. 1 and 2.

The first layer 10 includes a semi-insulating substrate. Here, "semi-insulating substrate" refers to a substrate formed by compound semiconductor and having the higher resistance (with specific resistance of $10^7$ Ω·cm or more). Specifically, the semi-insulating substrate forming the first layer 10 is a non-impurity-containing (undoped) GaAs substrate or InP substrate. The GaAs substrate (semi-insulating GaAs substrate) or the InP substrate (semi-insulating InP substrate) forming the first layer 10 may be in a stoichiometric condition. That is, Ga and As forming the GaAs substrate may exist at a ratio of 1:1 and In and P forming the InP substrate may exist at a ratio of 1:1. Note that the semi-insulating substrate forming the first layer 10 may be an InAs substrate or an InSb substrate.

The second layer 20 is located on the first layer 10. The photo conductive antenna 100 has a first region 3 in which the second layer 20 is formed on the first layer 10, and a second region 5 in which the second layer 20 is not formed on the first layer 10. In a plan view from a stacking direction of the first layer 10 and the second layer 20 (hereinafter, simply referred to as "in the plan view"), the first region 3 is a region overlapping with the second layer 20 and the second region 5 is a region not overlapping with the second layer 20.

An opening part 22 is formed in the second layer 20. The shape of the opening part 22 is not particularly limited, but a rectangular shape in the example shown in FIG. 2. The opening part 22 is formed to penetrate the second layer 20 so that a surface 11 of the first layer 10 may be exposed. That is, the bottom surface of the opening part 22 is defined by the surface 11. The second region 5 is a region overlapping with the opening part 22 in the plan view. In other words, the second region 5 is a region defined by the opening part 22. The second region 5 is located between the first electrode 30 and the second electrode 34 in the plan view.

The second layer 20 is formed using a material having the lower carrier mobility than the carrier mobility of the semi-insulating substrate forming the first layer 10. Here, "carrier mobility" refers to a distance at which, when carriers (electrons and holes) move in a solid material, the carriers move per unit time under the unit electric field intensity and ease of movement of the carriers in the solid material.

The material forming the second layer 20 specifically includes a semiconductor material having a recombination center and an insulating material such as silicon oxide or silicon nitride. Here, "recombination center" refers to an energy level depending on impurities and lattice defects other than donors and acceptors, and plays a role of mediation for recombination of electrons and holes. The specific resistance of the semiconductor material forming the second layer 20 is lower than the specific resistance of the semi-insulating substrate forming the first layer 10.

The semiconductor material forming the second layer is not particularly limited as long as it has the recombination center, and specifically, low-temperature growth GaAs (LT-GaAs), non-impurity-containing (undoped) GaAs (i-GaAs), or AlGaAs, oxygen-doped GaAs or InP.

Here, "LT-GaAs" refers to GaAs grown at the lower temperature, and when grown by MBE (Molecular Beam Epitaxy), the growth temperature is about 200° C. to 300° C. LT-GaAs contains excess As at about 1 atom % several digits larger than the solubility limit in the equilibrium state. The excess As is aggregated, and thereby, LT-GaAs has a defect as the recombination center. For example, GaAs having the recombination center may be formed by ion injection of As in GaAs in the stoichiometric condition.

In addition to LT-GaAs, InAs, AlAs, ZnTe, ZnSe containing aggregates may be used as semiconductor materials having recombination centers for the material forming the second layer 20.

The carrier mobility (electron mobility) of LT-GaAs is about 100 cm$^2$/Vs, the carrier lifetime (the time from generation to extinction of electrons) is about 0.2 ps, and the carrier saturation velocity (the velocity of electrons saturated for the electric field intensity) is about $3 \times 10^4$ m/s. On the other hand, the carrier mobility of semi-insulating GaAs is about 2000 cm$^2$/Vs, the carrier lifetime is about 200 ps, and the carrier saturation velocity is about $2 \times 10^5$ m/s. As described above, LT-GaAs has the lower carrier mobility than that of the semi-insulating GaAs. Note that the numeric values are just examples and may be changed depending on various conditions.

Figure 3:
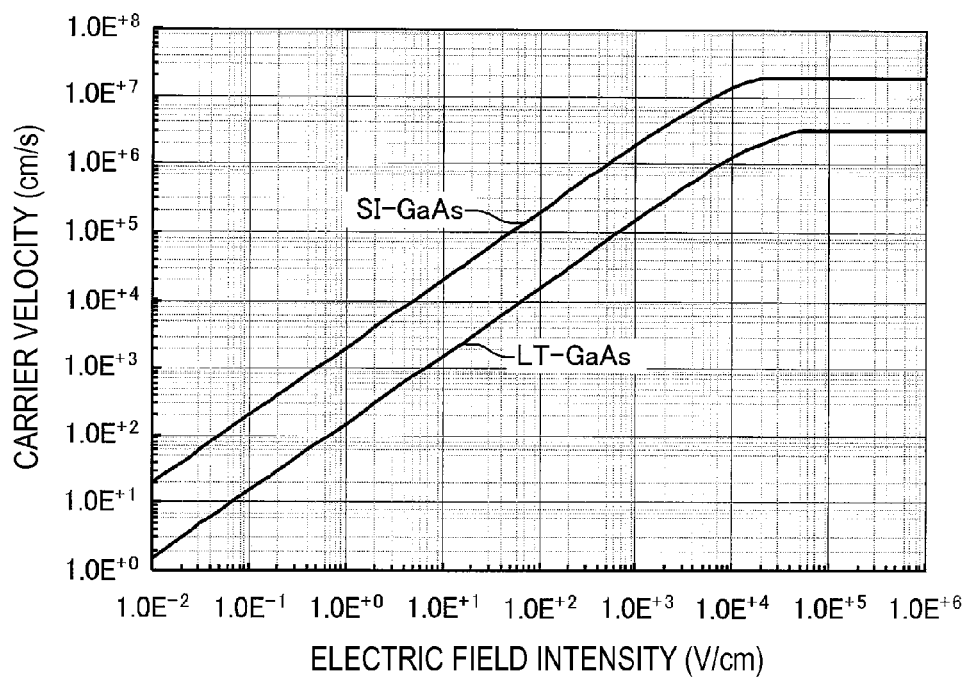
FIG. 3 is a graph showing relationships between electric field intensity and carrier velocity in low-temperature growth GaAs (LT-GaAs) and semi-insulating GaAs (SI-GaAs).
Figure 4:
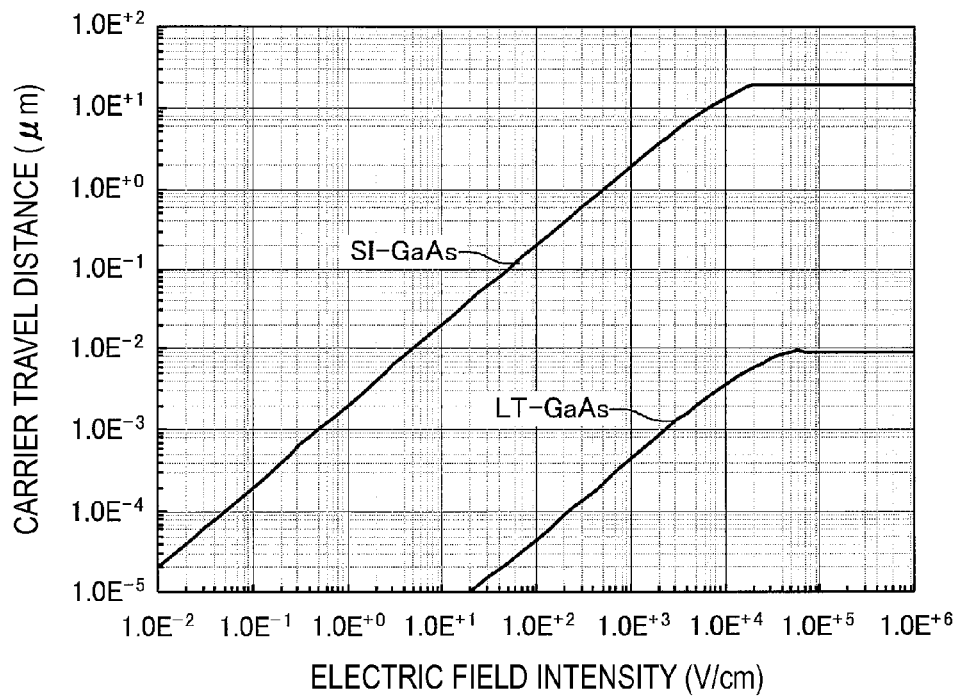
FIG. 4 is a graph showing relationships between electric field intensity and carrier travel distance in LT-GaAs and SI-GaAs.

Here, FIG. 3 is a graph showing relationships between electric field intensity and carrier velocity in LT-GaAs and semi-insulating GaAs (SI-GaAs). FIG. 4 is a graph showing relationships between electric field intensity and carrier travel distance in LT-GaAs and SI-GaAs. From FIGS. 3 and 4, it is known that SI-GaAs has the greater carrier velocity and carrier travel distance than those of LT-GaAs. Note that the carrier travel distance may be calculated by multiplication of the carrier velocity by the carrier lifetime.

The first electrode 30 and the second electrode 34 are located on the second layer 20 as shown in FIGS. 1 and 2. That is, the second layer 20 is located between the electrodes 30, 34 and the first layer 10. The electrodes 30, 34 are electrodes for applying a voltage to the first layer 10. The electrodes 30, 34 may apply a direct-current (DC) voltage to the first layer 10, or an alternating-current (AC) voltage to the first layer 10. The electrodes 30, 34 may be in ohmic contact with the second layer 20. The thickness of the second layer 20 is not particularly limited as long as a voltage may be applied to the first layer 10 by the electrodes 30, 34, and may be equal to or more than the minimum film thickness that can form the second layer 20. The thickness vary depending on the deposition method, and may be from several nanometers to 1 μm. The material of the electrodes 30, 34 is gold, platinum, titanium, aluminum, copper, chromium, or the like, for example. Note that, in the case of using gold, chromium is deposited and gold is formed thereon for increasing adhesion.

The first electrode 30 has a first projecting part 32 projecting from the first electrode 30 toward the second electrode 34 in the plan view. In the illustrated example, the first electrode 30 has a base part 33 and the first projecting part 32 projects from the base part 33. The second electrode 34 has a second projecting part 36 projecting from the second electrode 34 toward the first electrode 30 in the plan view. In the illustrated example, the second electrode 34 has a base part 37 and the second projecting part 36 projects from the base part 37. The electrodes 30, 34 may be line-symmetric with respect to an imaginary line (not shown) along a direction orthogonal to the direction from the first electrode 30 to the second electrode 34 and passing through the center C of a region 7 between the projecting parts 32, 36 in the plan view.

The planar shapes of the first projecting part 32 and the second projecting part 36 are rectangular shapes (i.e., dipole shapes) in the illustrated example, and not particularly limited, but may be trapezoidal shapes (i.e., bow-tie shapes), for example. Similarly, the planar shapes of the base parts 33, 37 are not limited to rectangular shapes. In the illustrated example, the region 7 between the first projecting part 32 and the second projecting part 36 in the plan view is the second region 5. That is, the first region 3 is not provided in the region 7 between the projecting parts 32, 36 in the plan view, and the first projecting part 32 has a side surface flush with the side surface of the second layer 20 defining the inner surface of the opening part 22 and the second projecting part 36 has a side surface flush with the side surface of the second layer 20 defining the inner surface of the opening part 22 as shown in FIG. 1.

The distance between the first projecting part 32 and the second projecting part 36 is from 1 μm to 100 μm, for example, and more specifically, about 5 μm. The spectrum of terahertz wave generated in the photo conductive antenna 100 (radiated from the photo conductive antenna 100) depends on the shapes of the electrodes 30, 34.

Next, the operation of the photo conductive antenna 100 will be explained. While the voltage is applied to the first layer 10 by the electrodes 30, 34, light pulse L is applied to the first layer of the second region 5. Here, "light pulse" refers to light having intensity steeply changed in a short period of time. The pulse width of the light pulse L (full width at half maximum FWHM) is not particularly limited, but from 1 fs (femtoseconds) to 800 fs, for example.

By application of the light pulse L, carriers (electrons and holes) are instantaneously generated in the first layer 10. The carriers are accelerated by the voltage applied by the electrodes 30, 34 and move, and a current (photocurrent) instantaneously flows in the first layer 10. Then, terahertz wave having a strength proportional to the temporal change of the photocurrent is generated. The temporal change of the photocurrent is proportional to the carrier mobility of the semi-insulating substrate forming the first layer 10. Therefore, in the photo conductive antenna 100, terahertz wave proportional to the carrier mobility of the semi-insulating substrate forming the first layer 10 is generated. Note that "terahertz wave" refers to electromagnetic wave having a frequency from 100 GHz to 30 THz, specifically, electromagnetic wave having a frequency from 300 GHz to 3 THz.

When a direct-current voltage is applied to the first layer 10 by the electrodes 30, 34 with the first electrode 30 as the positive electrode and the second electrode 34 as the negative electrode, it is preferable that the light pulse L is applied to the first electrode 30, not to the second electrode 34 as shown in FIGS. 1 and 2. That is, it is preferable that, in the plan view, the distance (minimum distance) between a carrier generation position P in which the light pulse L is applied and carriers are generated and the first electrode 30 is larger than the distance (minimum distance) between the carrier generation position P and the second electrode 34. The carriers (electrons) generated in the carrier generation position P move toward the first electrode 30 (positive electrode) side, and the distance between the carrier generation position P and the first electrode 30 is set to be larger, and thereby, the probability of extinction of electrons before reaching the first electrode 30 may be made higher.

For example, when the light pulse L is applied to the positive electrode side, the distance between the carrier generation position P and the positive electrode is smaller and the probability of the generated electrons reaching the positive electrode is higher. Accordingly, the withstand voltage may be lower.

Figure 5:
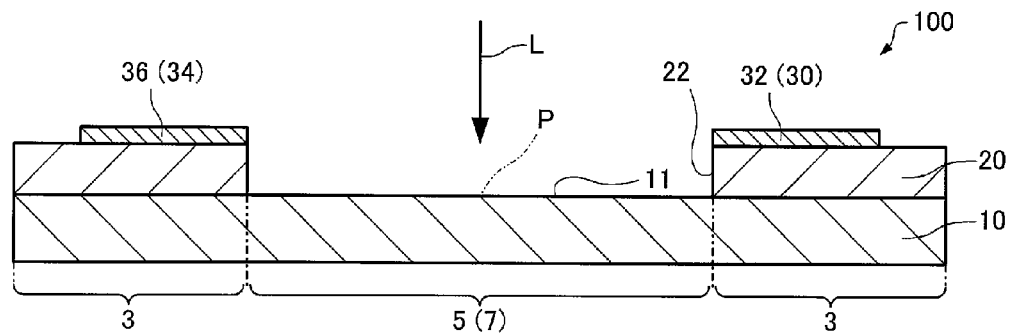
FIG. 5 is a sectional view schematically showing the photo conductive antenna according to the first embodiment.
Figure 6:
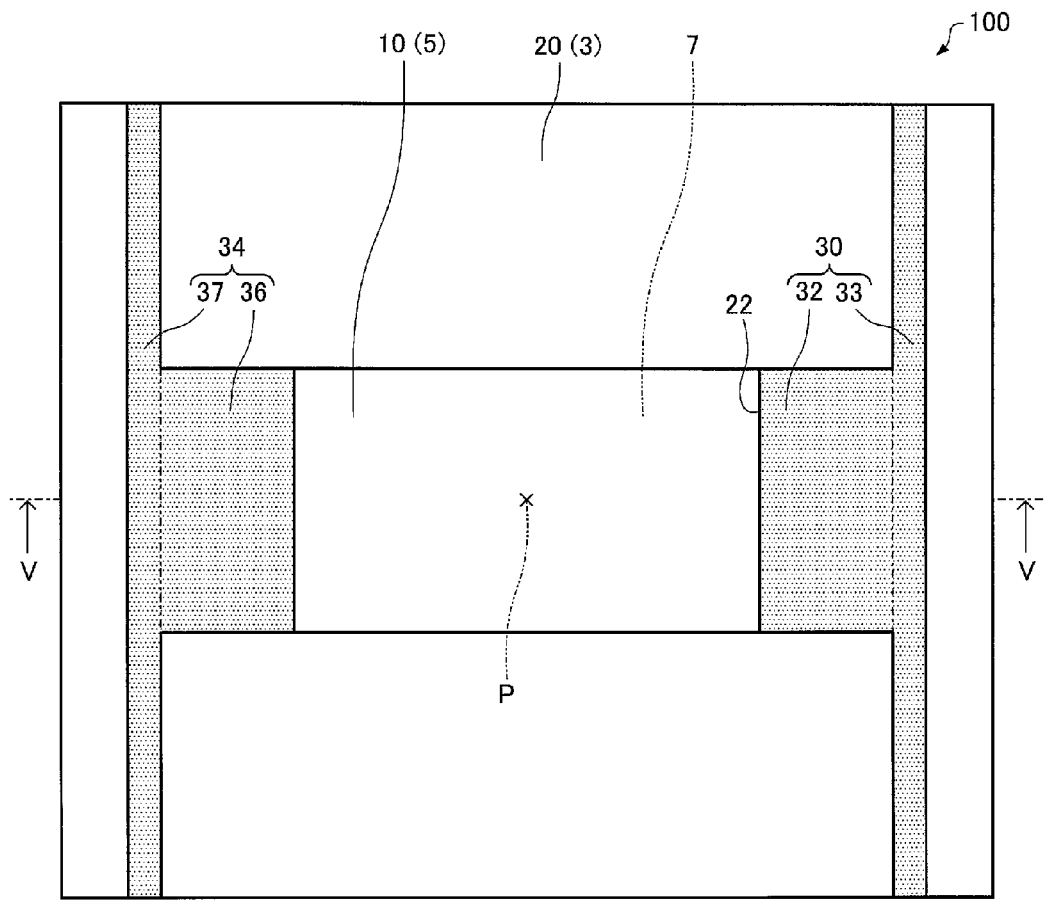
FIG. 6 is a plan view schematically showing the photo conductive antenna according to the first embodiment.

When an alternating-current voltage is applied to the first layer 10 by the electrodes 30, 34, it is preferable that the light pulse L is applied to the middle point between the electrodes 30, 34 in the plan view as shown in FIGS. 5 and 6. That is, it is preferable that, in the plan view, the distance between the carrier generation position P in which the light pulse L is applied and carriers are generated and the first electrode 30 is equal to the distance between the carrier generation position P and the second electrode 34. In the alternating-current voltage, the positive and negative electrodes are switched between the electrodes 30, 34. Accordingly, the travel direction of electrons is reversed. Therefore, the light pulse L is applied to the middle point between the electrodes 30, 34, and thereby, the probability of extinction of electrons generated in the carrier generation position P before reaching the positive electrode may be made higher.

For example, if the carrier generation position P is located at the one side of the electrodes 30, 34 (not at the middle point between the electrodes 30, 34), the distance between the carrier generation position P and the positive electrode may be smaller and the withstand voltage may be lower. Note that FIG. 5 is the sectional view along V-V line shown in FIG. 6.

The electron mobility of semi-insulating GaAs is larger than the electron mobility of LT-GaAs, and thus, it is particularly preferable to specify the position in which the light pulse L is applied (carrier generation position P) as described above in view of improvement in withstand voltage.

Note that, not limited to the examples shown in FIGS. 1 and 5, the light pulse L may be applied to a region 6 between the projecting parts 32, 36 in the plan view.

The photo conductive antenna 100 has the following advantages, for example.

According to the photo conductive antenna 100, the light pulse L is applied to the first layer 10 formed by the semi-insulating substrate. The carrier mobility of the semi-insulating substrate is larger than the carrier mobility of the material forming the second layer 20. Accordingly, the photo conductive antenna 100 may provide the higher carrier mobility and generate (radiate) terahertz wave with the higher strength than in the case where the light pulse L is applied to the second layer 20. More specifically, the photo conductive antenna 100 may generate terahertz wave with the higher strength by one digit or more than in the case where the light pulse L is applied to the second layer 20.

Further, in the photo conductive antenna 100, the second layer 20 is located between the first layer 10 and the electrodes 30, 34 and the second layer 20 is formed using the material having the lower carrier mobility than the carrier mobility of the semi-insulating substrate forming the first layer 10. Accordingly, the probability of the carriers (electrons) generated within the first layer 10 reaching the electrodes 30, 34 may be made lower. That is, with the second layer 20, the probability of extinction of the carriers generated within the first layer 10 before reaching the electrodes 30, 34 may be made higher. As a result, the photo conductive antenna 100 may have the higher withstand voltage. Furthermore, if the carriers reach the electrode, the spectrum of the terahertz wave generated in the photo conductive antenna may be deformed and a desired spectrum shape may not be obtained, however, the problem may be avoided in the photo conductive antenna 100.

According to the photo conductive antenna 100, the electrodes 30, 34 may apply the direct-current voltage to the first layer 10 and may apply the light pulse L to the second electrode 34 (negative electrode) side. Thereby, the probability of extinction of the electrons generated within the first layer 10 before reaching the first electrode 30 (positive electrode) may be made higher. As a result, the photo conductive antenna 100 may have the higher withstand voltage.

According to the photo conductive antenna 100, the electrodes 30, 34 may apply the alternating-current voltage to the first layer 10 and may apply the light pulse L to the middle point between the electrodes 30, 34. Thereby, the probability of extinction of the electrons generated within the first layer 10 before reaching the positive electrode may be made higher. As a result, the photo conductive antenna 100 may have the higher withstand voltage.

1.2. Method of Manufacturing Photo Conductive Antenna

Next, a method of manufacturing the photo conductive antenna according to the first embodiment will be explained with reference to the drawings. FIGS. 7 to 10 are sectional views schematically showing a manufacturing process of the photo conductive antenna 100 according to the first embodiment, and correspond to FIG. 1.

Figure 7:
FIG. 7 is a sectional view schematically showing a manufacturing process of the photo conductive antenna according to the first embodiment.

As shown in FIG. 7, the second layer 20 is formed on the first layer 10. The second layer 20 is formed by MBE or MOCVD (Metal Organic Chemical Vapor Deposition), for example. When the material forming the second layer 20 is LT-GaAs, the growth temperature by MBE is from 200° C. to 270° C., for example, and the growth temperature by MOCVD is from 400° C. to 700° C., for example. After the deposition of LT-GaAs by MBE or MOCVD, for example, heat treatment may be performed in an arsine atmosphere at from 600° C. to 800° C., for example. When LT-GaAs is deposited by MOCVD, the source of Ga may be TEGa (triethylgallium) and the source of As may be TBAs (tertiary butylarsine).

Figure 8:
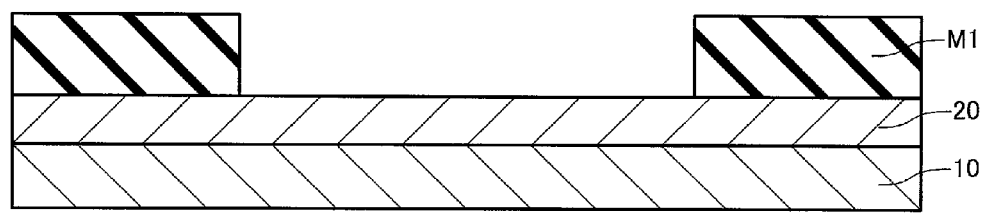
FIG. 8 is a sectional view schematically showing the manufacturing process of the photo conductive antenna according to the first embodiment.

As shown in FIG. 8, a mask layer M1 having a predetermined shape is formed on the second layer 20. The material of the mask layer M1 is photoresist or silicon oxide ($SiO_2$), for example. The mask layer M1 is formed by spin coating or CVD (Chemical Vapor Deposition), for example.

Figure 9:
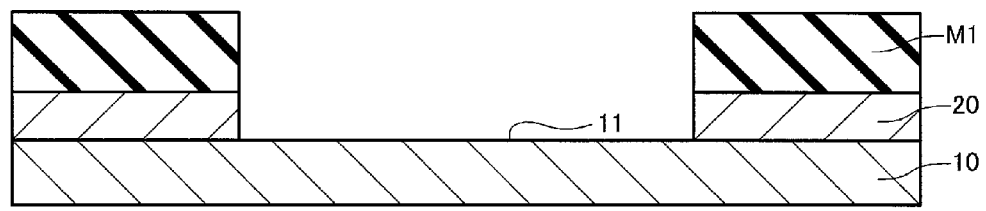
FIG. 9 is a sectional view schematically showing the manufacturing process of the photo conductive antenna according to the first embodiment.

As shown in FIG. 9, the second layer 20 is etched with the mask layer M1 as a mask, and the surface 11 of the first layer 10 is exposed. A slight removal of the first layer 10 by the etching is not problematic. Then, the mask layer M1 is removed by a known method, for example.

Figure 10:
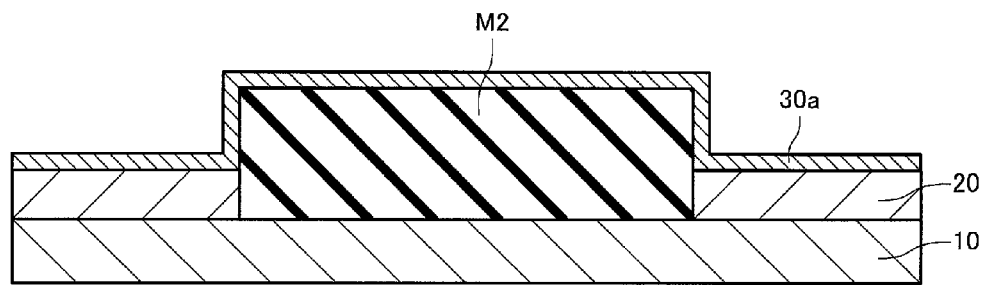
FIG. 10 is a sectional view schematically showing the manufacturing process of the photo conductive antenna according to the first embodiment.

As shown in FIG. 10, a mask layer M2 having a predetermined shape is formed on the exposed surface 11 of the first layer 10. The material and the forming method of the mask layer M2 may be the same as those of the mask layer M1. Then, an electrode layer 30a is formed on the mask layer M2 and the second layer 20. The electrode layer 30a is formed by vacuum evaporation, for example.

As shown in FIG. 1, the mask layer M2 is removed (lift-off) by a known method, for example. Thereby, the electrode layer 30a formed on the surface of the mask layer M2 is removed, and the electrodes 30, 34 may be formed.

In the above described process, the photo conductive antenna 100 may be manufactured.

Figure 11:
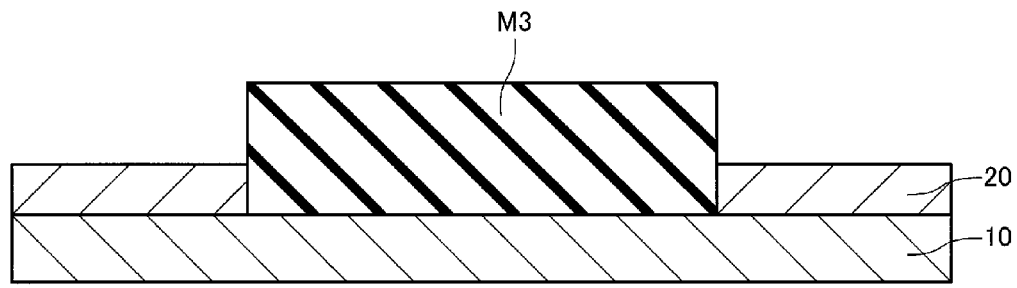
FIG. 11 is a sectional view schematically showing the manufacturing process of the photo conductive antenna according to the first embodiment.

Note that, in the method of forming the photo conductive antenna 100, as shown in FIG. 11, a mask layer M3 having a predetermined shape may be formed on the first layer 10 and the second layer 20 may be selectively epitaxially-grown on the surface 11 of the first layer 10 without the mask layer M3. The material and the forming method of the mask layer M3 may be the same as those of the mask layer M1.

1.3. Modified Example

Figure 12:
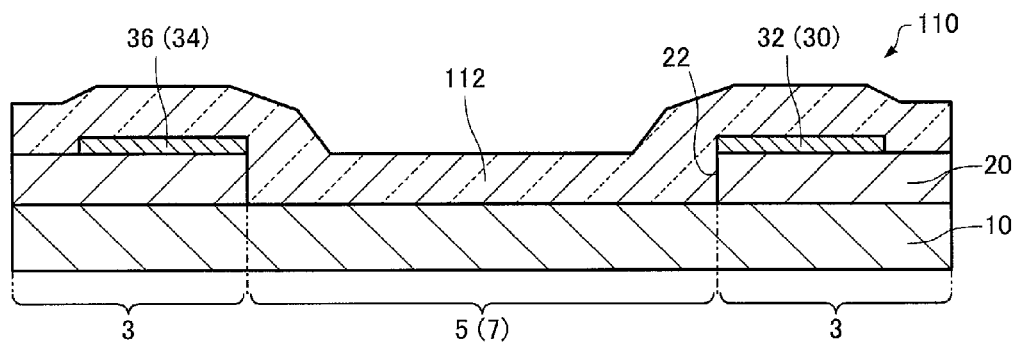
FIG. 12 is a sectional view schematically showing a photo conductive antenna according to a modified example of the first embodiment.

Next, a photo conductive antenna according to a modified example of the first embodiment will be explained with reference to the drawings. FIG. 12 is a sectional view schematically showing a photo conductive antenna 110 according to the modified example of the first embodiment and corresponds to FIG. 1. As below, in the photo conductive antenna 110, the members having the same functions as those of the component members of the above described photo conductive antenna 100 have the same signs and their detailed explanation will be omitted.

The photo conductive antenna 110 is different from the photo conductive antenna 100 in that a covering layer 112 is provided as shown in FIG. 12. The covering layer 112 is provided on the surface 11 of the first layer 10. More specifically, the covering layer 112 is provided in the region 7 (second region 5) between the first projecting part 32 and the second projecting part 36 in the plan view. In the illustrated example, the covering layer 112 is further provided on the surfaces of the electrodes 30, 34 and the surface of the second layer 20.

The covering layer 112 may transmit the light pulse L. The material of the covering layer 112 is silicon oxide ($SiO_2$), silicon nitride (SiN), or a resin, for example. The covering layer 112 is formed by CVD, for example.

According to the photo conductive antenna 110, generation of leak current may be suppressed by the covering layer 112, and the higher withstand voltage may be provided. For example, when the surface 11 of the first layer 10 is exposed, impurities may attach to the surface 11 and a leak path may be formed. As a result, leak current may be generated. In the photo conductive antenna 110, the problem may be avoided.

2. Second Embodiment

2.1. Photo Conductive Antenna

Figure 13:
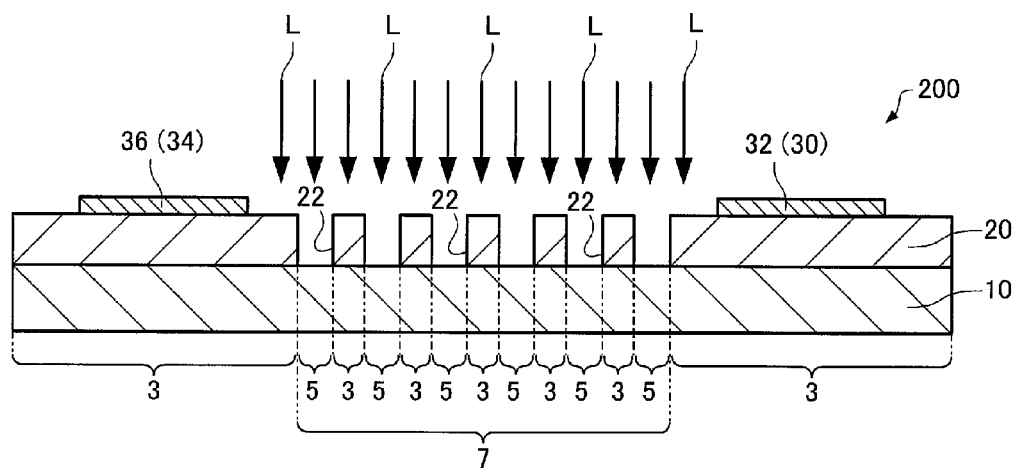
FIG. 13 is a sectional view schematically showing a photo conductive antenna according to the second embodiment.
Figure 14:
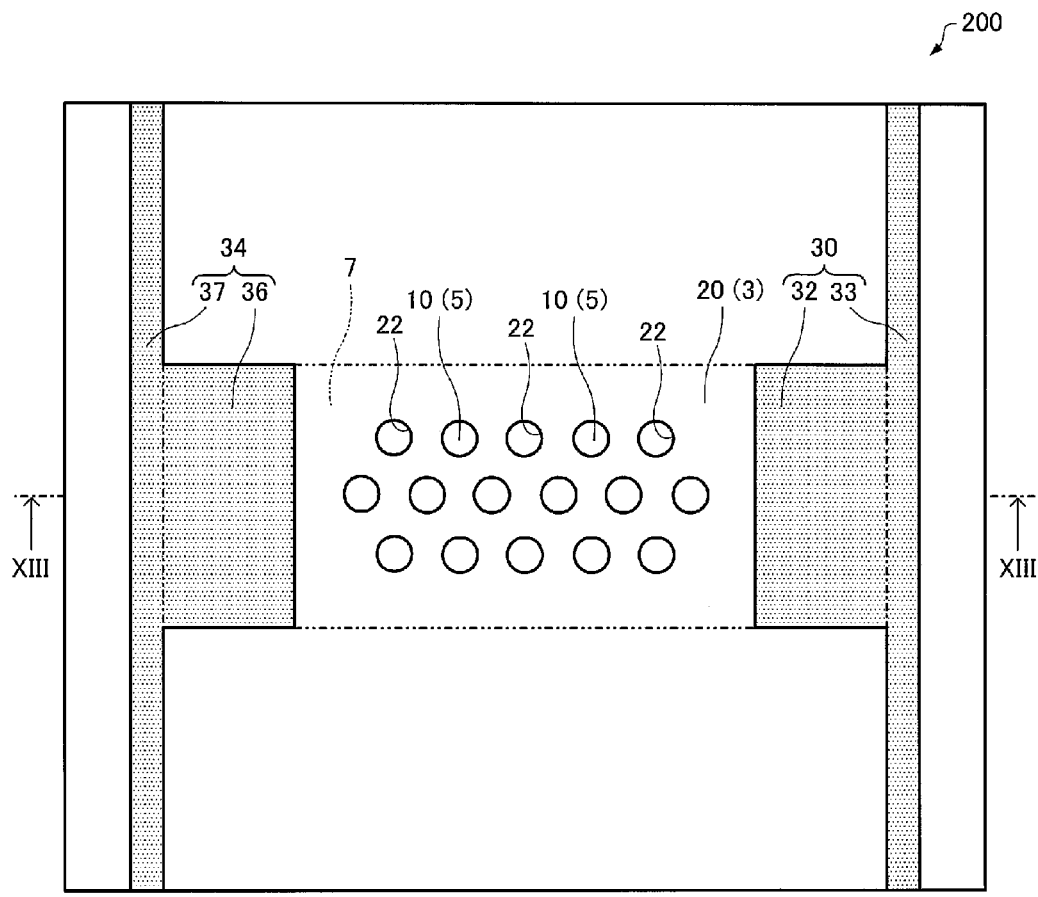
FIG. 14 is a plan view schematically showing the photo conductive antenna according to the second embodiment.

Next, a photo conductive antenna according to the second embodiment will be explained with reference to the drawings. FIG. 13 is a sectional view schematically showing a photo conductive antenna 200 according to the second embodiment. FIG. 14 is a plan view schematically showing the photo conductive antenna 200 according to the second embodiment. Note that FIG. 13 is the sectional view along XIII-XIII line of FIG. 14. As below, in the photo conductive antenna 200, the members having the same functions as those of the component members of the above described photo conductive antenna 100 have the same signs and their detailed explanation will be omitted.

In the photo conductive antenna 100, as shown in FIGS. 1 and 2, the region 7 between the first projecting part 32 and the second projecting part 36 in the plan view is the second region 5. That is, the first region 3 is not provided in the region 7 between the projecting parts 32, 36 in the plan view, and the first projecting part 32 has the side surface flush with the side surface of the second layer 20 defining the inner surface of the opening part 22 and the second projecting part 36 has the side surface flush with the side surface of the second layer 20 defining the inner surface of the opening part 22 as shown in FIG. 1.

On the other hand, in the photo conductive antenna 200, as shown in FIGS. 13 and 14, the first regions 3 and the second regions 5 are provided in the region 7 between the projecting parts 32, 36 in the plan view.

A plurality of the opening parts 22 defining the second regions 5 are provided. In the example shown in FIG. 14, 16 opening parts 22 are provided, however, the number is not particularly limited, but may be one. In the example shown in FIG. 14, the planar shape of the opening part 22 is a circular shape, however, the shape is not particularly limited, but may be a square shape, a pentagonal shape, a hexagonal shape, or an oval shape. The planar shapes of the plurality of the opening parts 22 may be the same or different from one another. Further, the positions of the opening parts 22 are not particularly limited, but, in the illustrated example, the plurality of the opening parts 22 are arranged so that the distances between the adjacent opening parts 22 may be equal.

In the photo conductive antenna 200, the light pulse L may be applied to the entire region 7 between the projecting parts 32, 36 in the plan view as shown in FIG. 13. Thereby, carries may be generated in the first layer 10 and the second layer 20. Note that, though not illustrated, the light pulse L may be selectively applied to the second regions 5.

According to the photo conductive antenna 200, the size and the number of the opening parts 22 are changed, and thereby, the area of the first layer 10 irradiated with the light pulse L may be adjusted. Therefore, the size and the number of the opening parts 22 are changed, and thereby, the strength of the terahertz wave radiated from the photo conductive antenna 200 may be controlled. Further, in the photo conductive antenna 200, the size and the intervals of the opening parts 22 are changed, and thereby, the frequency of the terahertz wave radiated from the photo conductive antenna 200 may be controlled.

2.2. Method of Manufacturing Photo Conductive Antenna

Next, a method of manufacturing the photo conductive antenna according to the second embodiment will be explained. The method of manufacturing the photo conductive antenna 200 according to the second embodiment is basically the same as the above described method of manufacturing the photo conductive antenna 100. Therefore, the detailed explanation thereof will be omitted.

2.3. Modified Examples

2.3.1. First Modified Example

Figure 15:
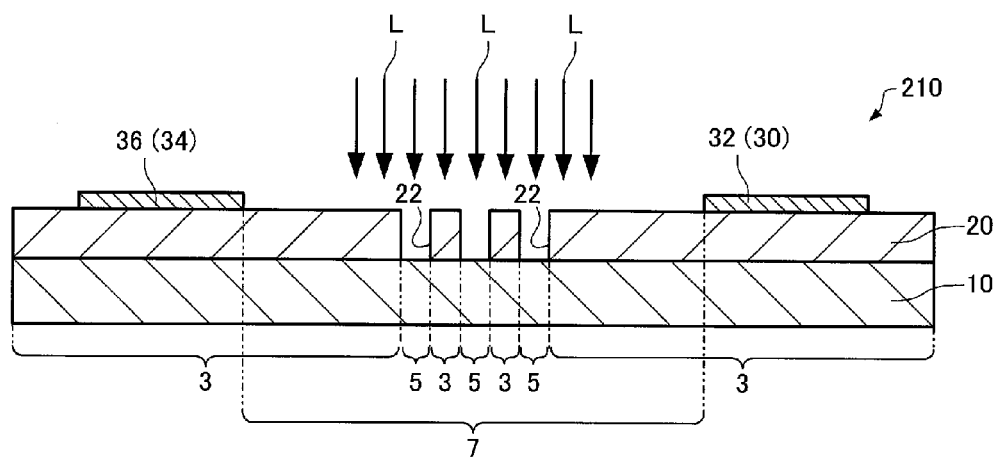
FIG. 15 is a sectional view schematically showing a photo conductive antenna according to a first modified example of the second embodiment.
Figure 16:
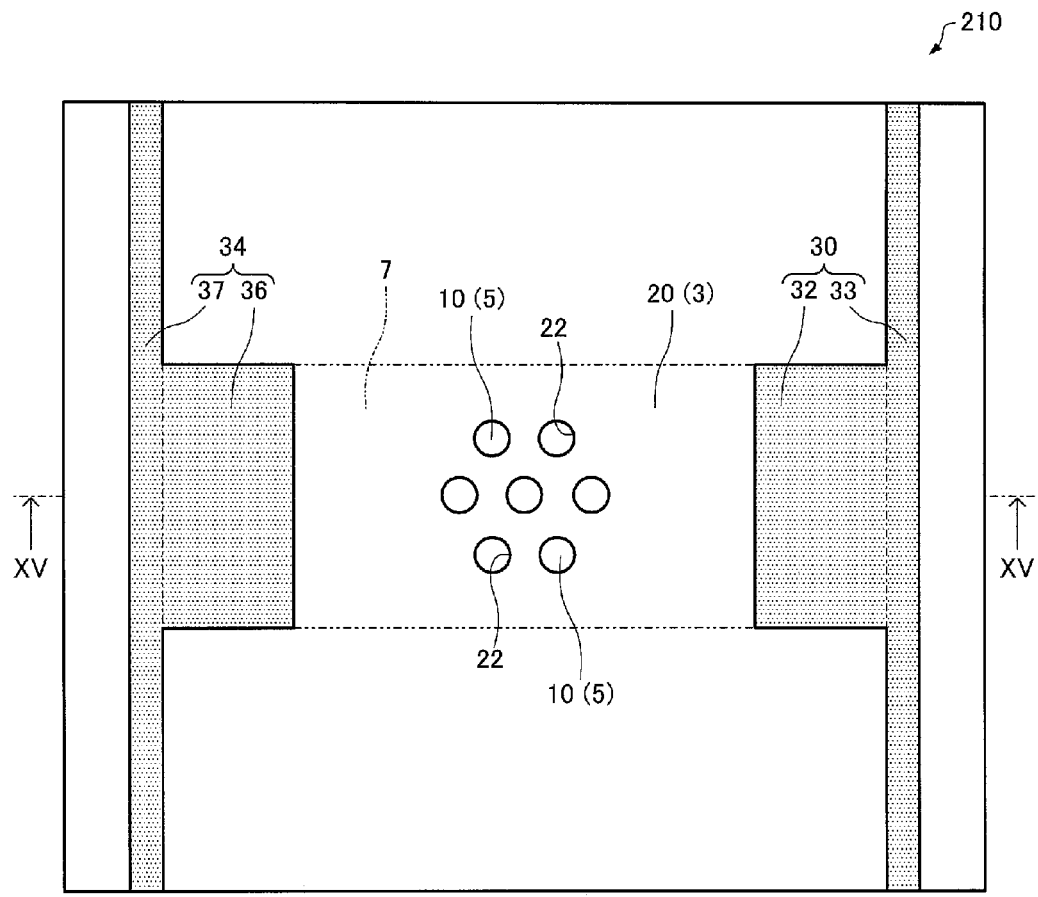
FIG. 16 is a plan view schematically showing the photo conductive antenna according to the first modified example of the second embodiment.

Next, a photo conductive antenna according to a first modified example of the second embodiment will be explained with reference to the drawings. FIG. 15 is a sectional view schematically showing a photo conductive antenna 210 according to the first modified example of the second embodiment. FIG. 16 is a plan view schematically showing the photo conductive antenna 210 according to the first modified example of the second embodiment. Note that FIG. 15 is the sectional view along XV-XV line of FIG. 14.

As below, in the photo conductive antenna 210, the members having the same functions as those of the component members of the above described photo conductive antennas 100, 200 have the same signs and their detailed explanation will be omitted. This applies to photo conductive antennas 220, 230, 240 according to the following modified examples.

In the photo conductive antenna 210, as shown in FIGS. 15 and 16, the opening parts 22 defining the second regions 5 are not formed near the projecting parts 32, 36 compared to the photo conductive antenna 200. Specifically, when the distance between the projecting parts 32, 36 is about 5 µm, in the photo conductive antenna 210, in the plan view, the distance (minimum distance) between the first projecting part 32 and the opening part 22 and the distance (minimum distance) between the second projecting part 36 and the opening part 22 are apart by about 2 µm or more (about four tenth of the distance between the projecting parts 32, 36).

According to the photo conductive antenna 210, the distances from the generation position of the carriers generated within the first layer 10 by irradiation of the light pulse L to the electrodes 30, 34 may be made longer compared to the photo conductive antenna 200. Accordingly, the probability of the carriers generated within the first layer 10 before reaching the electrodes 30, 34 may be made higher. As a result, the photo conductive antenna 210 may have the higher withstand voltage.

2.3.2. Second Modified Example

Figure 17:
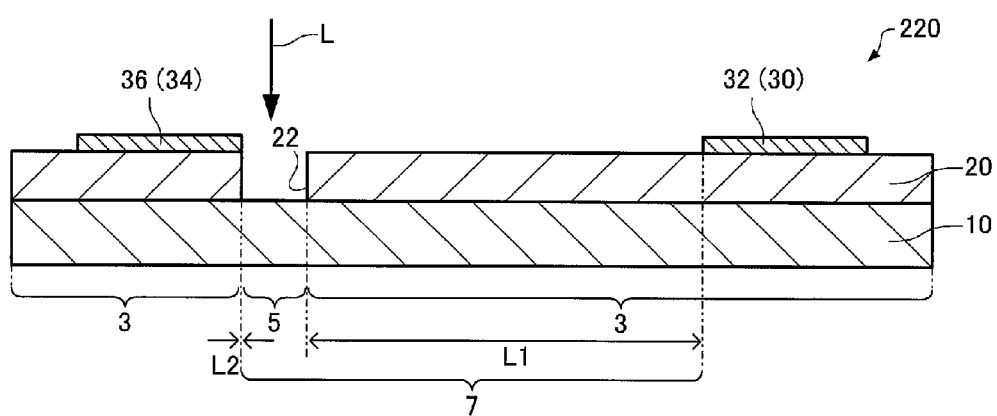
FIG. 17 is a sectional view schematically showing a photo conductive antenna according to a second modified example of the second embodiment.
Figure 18:
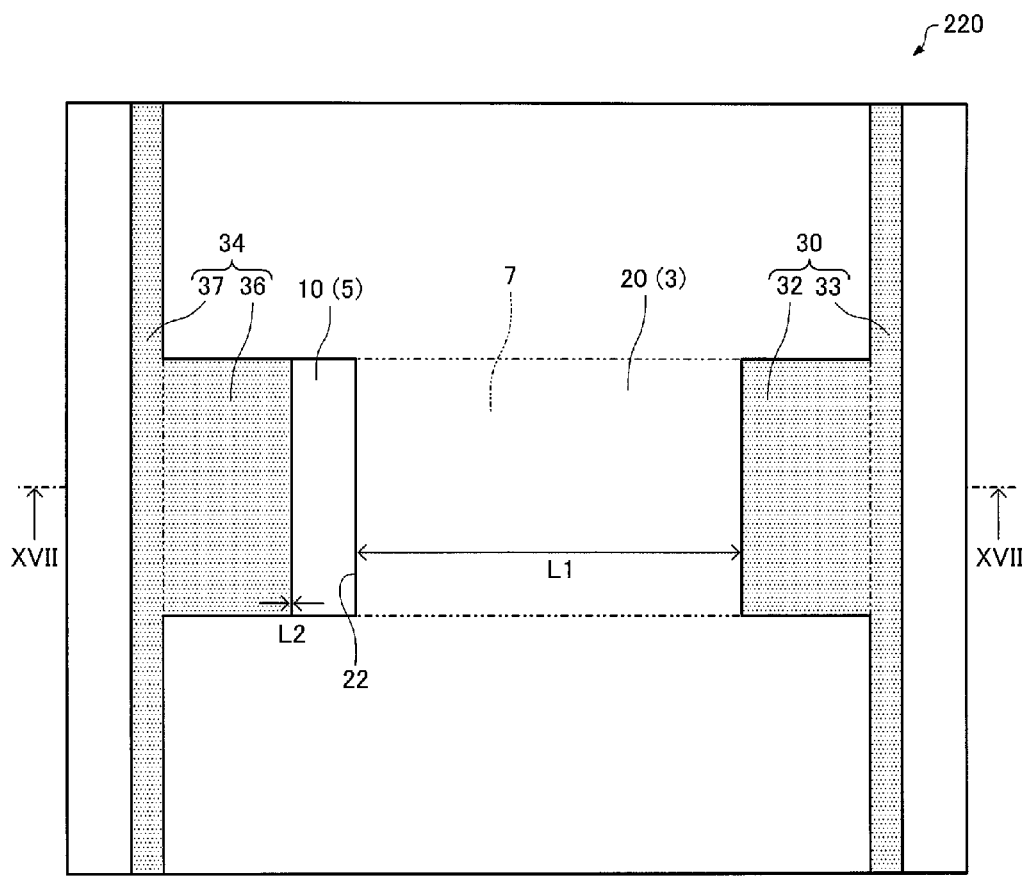
FIG. 18 is a plan view schematically showing the photo conductive antenna according to the second modified example of the second embodiment.

Next, a photo conductive antenna according to a second modified example of the second embodiment will be explained with reference to the drawings. FIG. 17 is a sectional view schematically showing a photo conductive antenna 220 according to the second modified example of the second embodiment. FIG. 18 is a plan view schematically showing the photo conductive antenna 220 according to the second modified example of the second embodiment. Note that FIG. 17 is the sectional view along XVII-XVII line of FIG. 18.

In the photo conductive antenna 200, as shown in FIGS. 13 and 14, the plurality of opening parts 22 (second regions 5) are provided. On the other hand, in the photo conductive antenna 220, as shown in FIGS. 17 and 18, for example, one opening part 22 (second region 5) is provided.

In the photo conductive antenna 220, in the plan view, the distance (minimum distance) L1 between the second region 5 and the first projecting part 32 is larger than the distance (minimum distance) L2 between the second region 5 and the second projecting part 36. That is, the second region 5 is provided closer to the second projecting part 36 than the first projecting part 32. In the illustrate example, the distance L2 is zero. That is, the second projecting part 36 has a side surface flush with the side surface of the second layer 20 defining the inner surface of the opening part 22. In other words, the second projecting part 36 is in contact with the opening part 22 in the plan view.

Note that, though not illustrated, the second projecting part 36 has no side surface flush with the side surface of the second layer 20 defining the inner surface of the opening part 22, and the projecting part 36 may be apart from the opening part 22 in the plan view.

Further, though not illustrated, if the distance L1 is larger than the distance L2, a plurality of the opening parts 22 (second regions 5) may be provided in the region 7 between the projecting parts 32, 36 in the plan view.

In the photo conductive antenna 220, the electrodes 30, 34 apply a direct-current voltage to the first layer 10. The first electrode 30 is a positive electrode and the second electrode 34 is a negative electrode.

According to the photo conductive antenna 220, the carriers (electrons) generated within the first layer 10 move toward the first electrode 30 (positive electrode) side. Therefore, in the photo conductive antenna 220, the distance L1 is set to be larger than the distance L2, and thereby, the probability of extinction of electrons generated within the first layer 10 before reaching the first electrode 30 (positive electrode) may be made higher. As a result, the photo conductive antenna 220 may have the higher withstand voltage.

2.3.3. Third Modified Example

Figure 19:
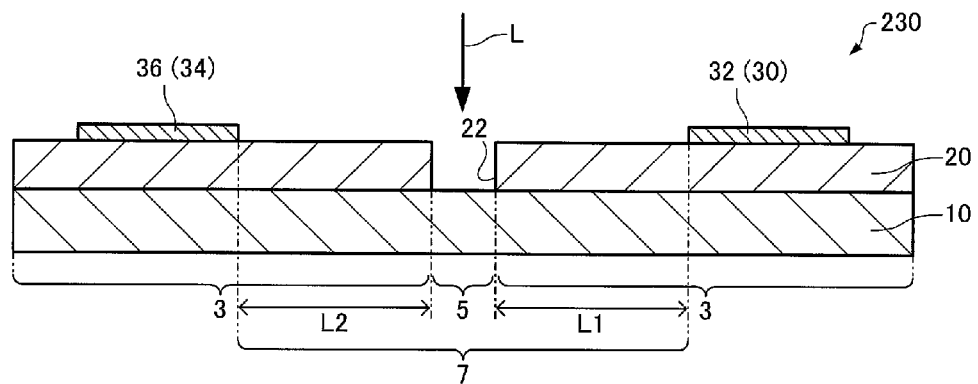
FIG. 19 is a sectional view schematically showing a photo conductive antenna according to a third modified example of the second embodiment.
Figure 20:
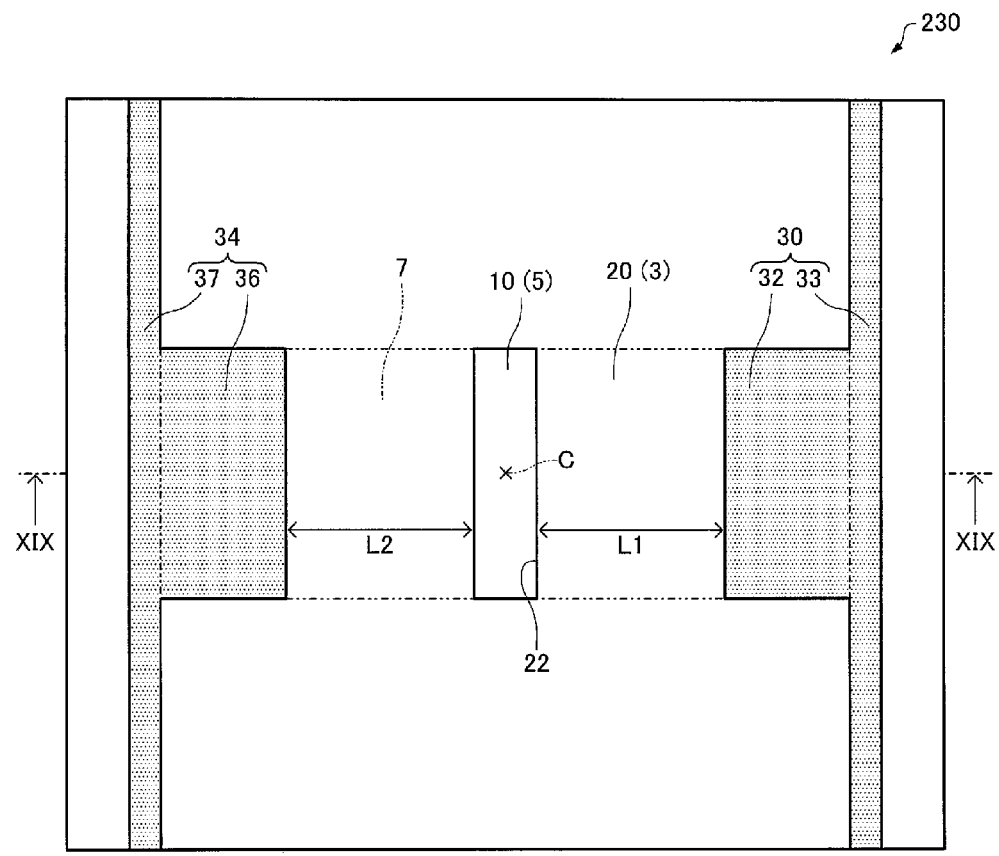
FIG. 20 is a plan view schematically showing the photo conductive antenna according to the third modified example of the second embodiment.

Next, a photo conductive antenna according to a third modified example of the second embodiment will be explained with reference to the drawings. FIG. 19 is a sectional view schematically showing a photo conductive antenna 230 according to the third modified example of the second embodiment. FIG. 20 is a plan view schematically showing the photo conductive antenna 230 according to the third modified example of the second embodiment. Note that FIG. 19 is the sectional view along XIX-XIX line of FIG. 20.

In the photo conductive antenna 200, as shown in FIGS. 13 and 14, the plurality of opening parts 22 (second regions 5) are provided. On the other hand, in the photo conductive antenna 20, as shown in FIGS. 19 and 20, for example, one opening part 22 (second region 5) is provided.

In the photo conductive antenna 230, in the plan view, the distance (minimum distance) L1 between the second region 5 and the first projecting part 32 is equal to the distance (minimum distance) L2 between the second region 5 and the second projecting part 36. In the illustrated example, the second region 5 (opening part 22) is provided to overlap with the center C of the region 7 between the projecting parts 32, 36 in the plan view.

Note that, though not illustrated, if the distance L1 is equal to the distance L2, a plurality of the opening parts 22 (second regions 5) may be provided in the region 7 between the projecting parts 32, 36 in the plan view.

In the photo conductive antenna 230, the electrodes 30, 34 apply an alternating-current voltage to the first layer 10. That is, in the photo conductive antenna 230, the positive and negative electrodes are switched between the electrodes 30, 34.

According to the photo conductive antenna 230, the travel direction of the electrons generated within the first layer 10 is reversed. Therefore, the distance L1 and the distance L2 are set to be equal, and thereby, the probability of extinction of electrons generated within the first layer 10 before reaching the positive electrode may be made higher. As a result, the photo conductive antenna 230 may have the higher withstand voltage.

2.3.4. Fourth Modified Example

Figure 21:
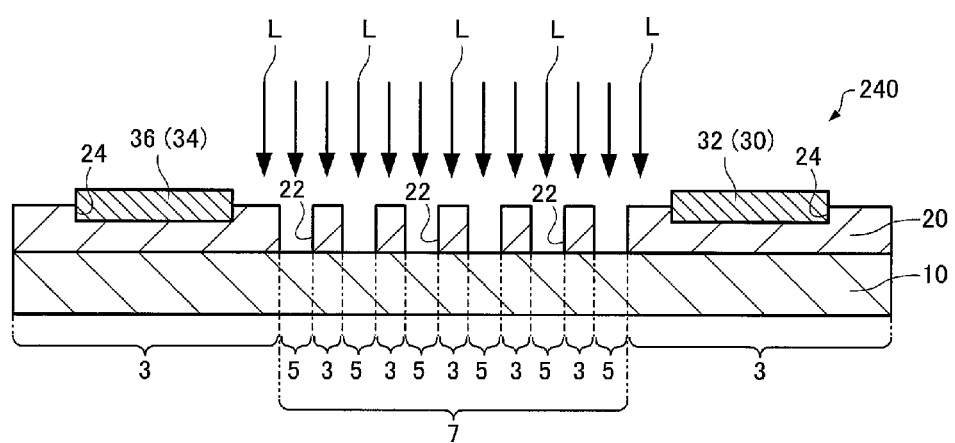
FIG. 21 is a sectional view schematically showing a photo conductive antenna according to a fourth modified example of the second embodiment.

Next, a photo conductive antenna according to a fourth modified example of the second embodiment will be explained with reference to the drawings. FIG. 21 is a sectional view schematically showing a photo conductive antenna 240 according to the fourth modified example of the second embodiment, and corresponds to FIG. 13.

The photo conductive antenna 240 is different from the photo conductive antenna 200 in that recessed parts 24 are formed in the second layer 20 as shown in FIG. 21. The bottom surfaces of the recessed parts 24 are defined by the second layer 20. The recessed parts 24 are formed by photolithography and etching, for example.

In the photo conductive antenna 240, the electrodes 30, 34 are provided in the recessed parts 24. That is, the thickness of the second layer 20 located under the electrodes 30, 34 is smaller than the thickness of the second layer 20 not located under the electrodes 30, 34. The entire electrodes 30, 34 may be provided in the recessed parts 24, or only the projecting parts 32, 36 of the electrodes 30, 34 may be provided in the recessed parts 24. The planar shapes of the recessed parts 24 are not particularly limited as long as they may overlap with the projecting parts 32, 36.

According to the photo conductive antenna 240, the electrodes 30, 34 are provided in the recessed parts 24, and thereby, the voltage applied to the first layer 10 by the electrodes 30, 34 may be made higher compared to the photo conductive antenna 200. Accordingly, the photo conductive antenna 240 may generate terahertz wave with the higher strength.

2.3.5. Fifth Modified Example

Figure 22:
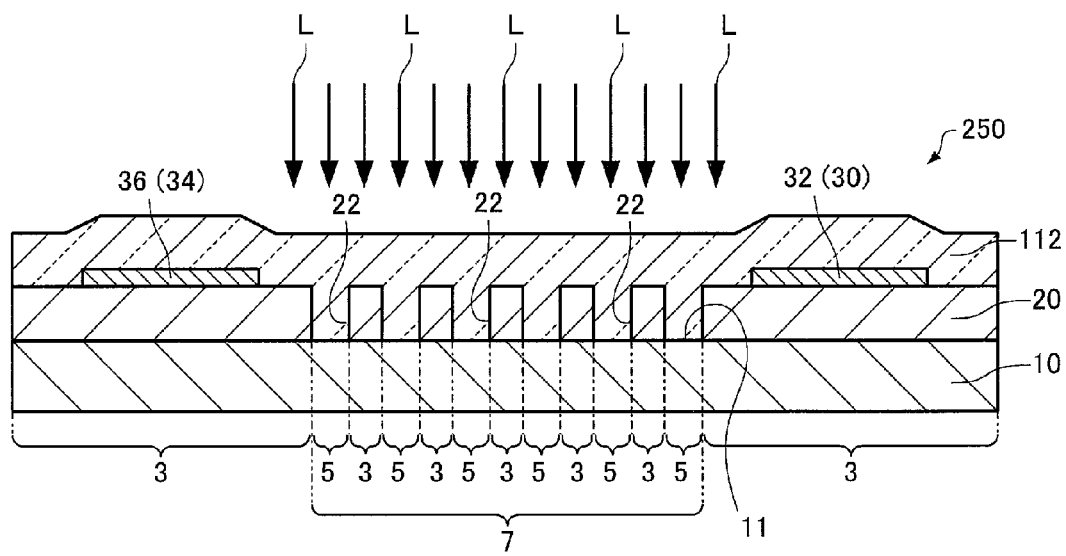
FIG. 22 is a sectional view schematically showing a photo conductive antenna according to a fifth modified example of the second embodiment.

Next, a photo conductive antenna according to a fifth modified example of the second embodiment will be explained with reference to the drawings. FIG. 22 is a sectional view schematically showing a photo conductive antenna 250 according to the fifth modified example of the second embodiment, and corresponds to FIG. 13. As below, in the photo conductive antenna 250, the members having the same functions as those of the component members of the above described photo conductive antennas 100, 110, 200 have the same signs and their detailed explanation will be omitted.

The photo conductive antenna 250 is different from the photo conductive antenna 200 in that a covering layer 112 is provided as shown in FIG. 22. The covering layer 112 is provided on the surface 11 of the first layer 10. In the illustrated example, the covering layer 112 is further provided on the surface of the second layer 20 and the surfaces of the electrodes 30, 34.

According to the photo conductive antenna 250, generation of leak current may be suppressed by the covering layer 112, and the higher withstand voltage may be provided. For example, when the surface 11 of the first layer 10 is exposed, impurities may attach to the surface 11 and a leak path may be formed. As a result, leak current may be generated. In the photo conductive antenna 250, the problem may be avoided.

3. Third Embodiment

Figure 23:
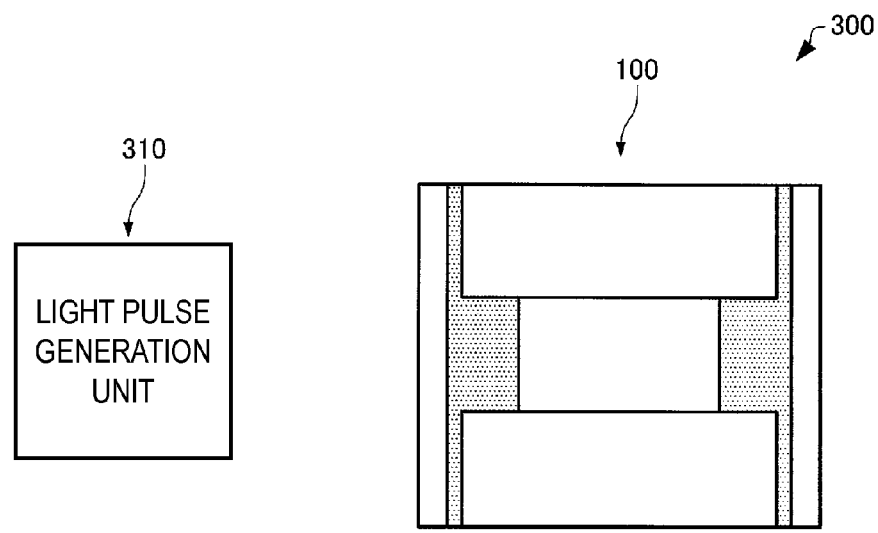
FIG. 23 schematically shows a terahertz wave generator according to the third embodiment.

Next, a terahertz wave generator according to the third embodiment will be explained with reference to the drawings. FIG. 23 schematically shows a terahertz wave generator 300 according to the third embodiment.

The terahertz wave generator 300 includes a light pulse generation unit 310 and the photo conductive antenna according to the invention as shown in FIG. 23. As below, an example using the photo conductive antenna 100 as the photo conductive antenna according to the invention will be explained.

The light pulse generation unit 310 generates light pulse as excitation light. The light pulse generation unit 310 may irradiate the photo conductive antenna 100. The width of the light pulse generated by the light pulse generation unit 310 is from 1 fs to 800 fs, for example. As the light pulse generation unit 310, for example, a femtosecond fiber laser or a titanium-sapphire laser is used.

The photo conductive antenna 100 is irradiated with the light pulse as described above, and thereby, may generate terahertz wave.

The terahertz wave generator 300 includes the photo conductive antenna 100, and thereby, may generate terahertz wave with the higher strength.

4. Fourth Embodiment

Figure 24:
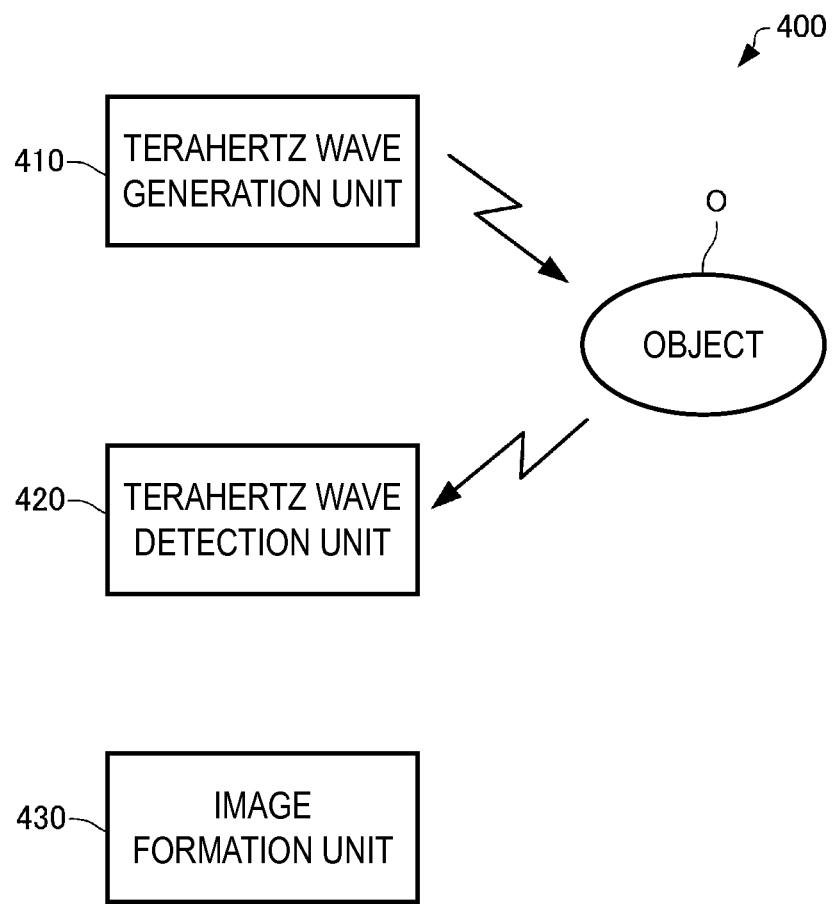
FIG. 24 is a block diagram schematically showing an imaging apparatus according to the fourth embodiment.
Figure 25:
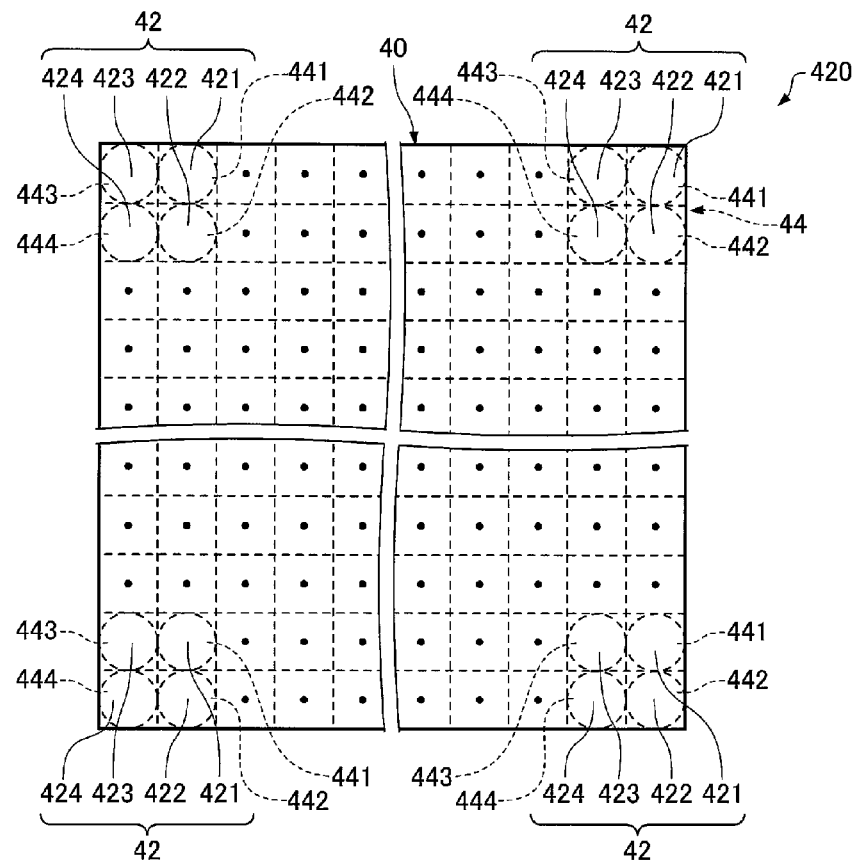
FIG. 25 is a plan view schematically showing a terahertz wave detection unit of the imaging apparatus according to the fourth embodiment.
Figure 26:
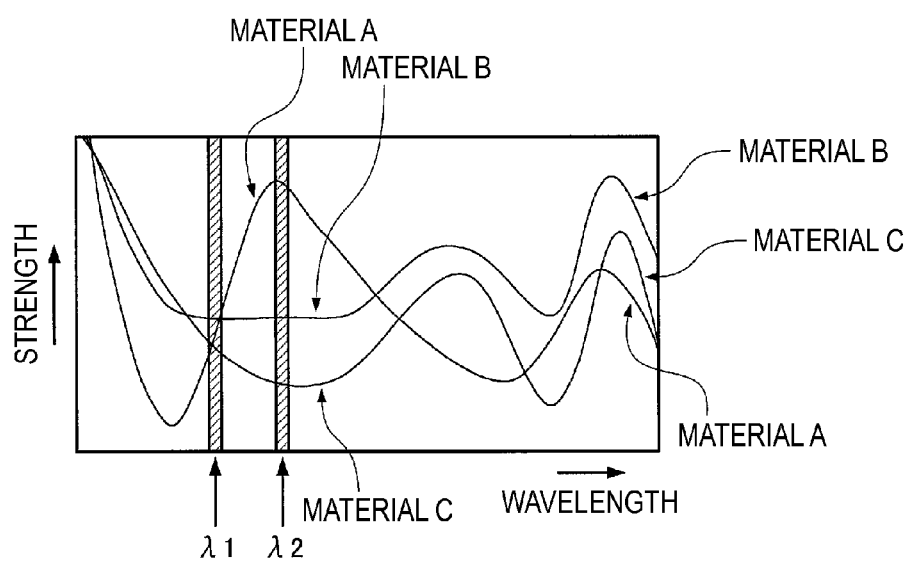
FIG. 26 is a graph showing spectra at a terahertz band of objects.
Figure 27:
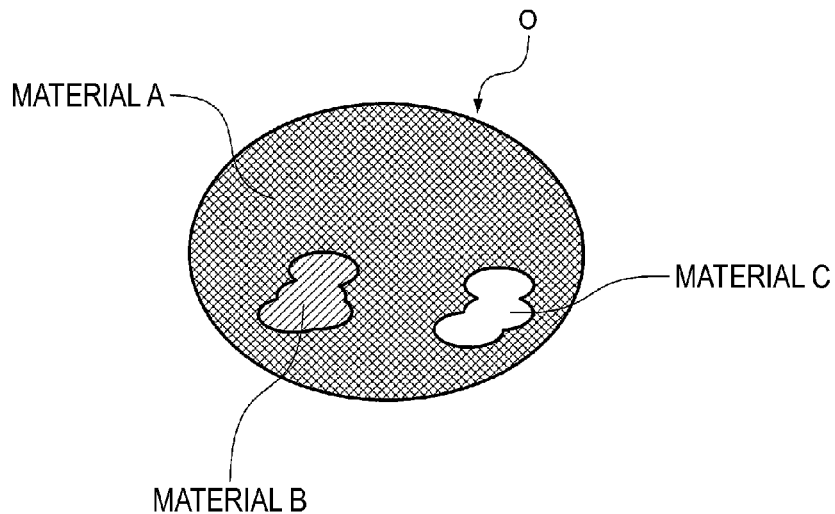
FIG. 27 is an image showing distributions of materials A, B, and C of the object.

Next, an imaging apparatus 400 according to the fourth embodiment will be explained with reference to the drawings. FIG. 24 is a block diagram showing the imaging apparatus 400 according to the fourth embodiment. FIG. 25 is a plan view schematically showing a terahertz wave detection unit 420 of the imaging apparatus 400. FIG. 26 is a graph showing spectra at a terahertz band of objects. FIG. 27 is an image showing distributions of materials A, B, and C of the object.

The imaging apparatus 400 includes a terahertz wave generation unit 410 that generates terahertz wave, a terahertz wave detection unit 420 that detects terahertz wave output from the terahertz wave generation unit 410 and transmitted through an object O or reflected by the object O, and an image formation unit 430 that generates an image of the object O, i.e., image data based on the detection result of the terahertz wave detection unit 420 as shown in FIG. 24.

As the terahertz wave generation unit 410, the terahertz wave generator according to the invention may be used. As below, the case of using the terahertz wave generator 300 as the terahertz wave generator according to the invention will be explained.

As the terahertz wave detection unit 420, a unit including a filter 40 that allows terahertz wave having target wavelengths to pass, and detection parts 44 that detect the terahertz wave having the target wavelengths that have passed through the filter 40. Further, as the detection part 44, for example, a part that converts and detects terahertz wave into heat, i.e., a part that may convert terahertz wave into heat and detect the energy (strength) of the terahertz wave is used. The detection part includes a pyroelectric sensor, a bolometer, or the like, for example. Note that the configuration of the terahertz wave detection unit 420 is not limited to the above described configuration.

Further, the filter 40 has a plurality of pixels (unit filter parts) 42 two-dimensionally arranged. That is, the respective pixels 42 are arranged in a matrix.

Furthermore, each pixel 42 has a plurality of areas that pass terahertz waves having different wavelengths from one another, i.e., a plurality of areas through which wavelengths of terahertz wave to be passed (hereinafter, also referred to as "passage wavelengths") are different from one another. Note that, in the illustrated configuration, each pixel 42 has a first area 421, a second area 422, a third area 423, and a fourth area 424.

In addition, the detection part 44 has a first unit detection portion 441, a second unit detection portion 442, a third unit detection portion 443, and a fourth unit detection portion 444 respectively provided in correspondence with the first area 421, the second area 422, the third area 423, and the fourth area 424 of each pixel 42 of the filter 40. Each first unit detection portion 441, each second unit detection portion 442, each third unit detection portion 443, and each fourth unit detection portion 444 convert and detect the terahertz waves that have passed the first area 421, the second area 422, the third area 423, and the fourth area 424 of each pixel 42 into heat, respectively. Thereby, in each pixel 42, the terahertz waves having the four target wavelengths may be respectively and reliably detected.

Next, a usage example of the imaging apparatus 400 will be explained.

First, suppose that the object O to be spectroscopically imaged includes three materials A, B, and C. The imaging apparatus 400 performs spectroscopic imaging of the object O. Further, here, as an example, the terahertz wave detection unit 420 detects the terahertz waves reflected by the object O.

Furthermore, in each pixel 42 of the filter 40 of the terahertz wave detection unit 420, the first area 421 and the second area 422 are used. Suppose that the passage wavelength of the first area 421 is $\lambda 1$ and the passage wavelength of the second area 422 is $\lambda 2$, and the strength of the component of the wavelength $\lambda 1$ of the terahertz wave reflected by the object O is $\alpha 1$ and the strength of the component of the wavelength $\lambda 2$ is $\alpha 2$, the passage wavelength $\lambda 1$ of the first area 421 and the passage wavelength $\lambda 2$ of the second area 422 are set so that the difference ($\alpha 2 - \alpha 1$) between the strength $\alpha 2$ and the strength $\alpha 1$ may be significantly distinguished among the material A, the material B, and the material C.

As shown in FIG. 26, in the material A, the difference ($\beta 2 - \alpha 1$) between the strength $\alpha 2$ of the component of the wavelength $\lambda 2$ and the strength al of the component of the wavelength $\lambda 1$ of the terahertz wave reflected by the object O takes a positive value. Further, in the material B, the difference ($\alpha 2 - \alpha 1$) between the strength $\alpha 2$ and the strength $\alpha 1$ is zero. Furthermore, in the material C, the difference ($\alpha 2 - \alpha 1$) between the strength $\alpha 2$ and the strength al takes a negative value.

When the spectroscopic imaging of the object O is performed using the imaging apparatus 400, first, terahertz wave is generated by the terahertz wave generation unit 410, and the terahertz wave is applied to the object O. Then, the terahertz wave reflected by the object O is detected as α1 and α2 by the terahertz wave detection unit 420. The detection result is sent out to the image formation unit 430. Note that the application of the terahertz wave to the object O and the detection of the terahertz wave reflected by the object O are performed with respect to the entire object O.

In the image formation unit 430, the difference (α2−α) between the strength α2 of the component of the wavelength λ2 of the terahertz wave that has passed through the second area 422 of the filter 40 and the strength α1 of the component of the wavelength λ1 of the terahertz wave that has passed through the first area 421 is obtained based on the detection result. Then, of the object O, the section in which the difference takes a positive value is specified as the material A, the section in which the difference is zero is specified as the material B, and the section in which the difference takes a negative value is specified as the material C.

Further, in the image formation unit 430, as shown in FIG. 27, the image data of an image showing distributions of the materials A, B, and C of the object O is created. The image data is sent out to a monitor (not shown) from the image formation unit 430, and the image showing distributions of the materials A, B, and C of the object O is displayed on the monitor. In this case, for example, the distributions are displayed in different colors, the area of the material A of the object O in black, the area of the material B in gray, and the area of the material C in white. In the imaging apparatus 400, as described above, the identification of the respective materials forming the object O and the distribution measurement of the respective materials may be performed at the same time.

Note that the usage of the imaging apparatus 400 is not limited to the above described usage. For example, terahertz wave is applied to a person, the terahertz wave transmitted through or reflected by the person is detected, the processing is performed in the image formation unit 430, and thereby, whether or not the person possesses a gun, a knife, illegal drug, or the like may be determined.

According to the imaging apparatus 400, the photo conductive antenna 100 that can generate terahertz wave with the higher strength is provided. Accordingly, the imaging apparatus 400 may have the higher detection sensitivity.

5. Fifth Embodiment

Figure 28:
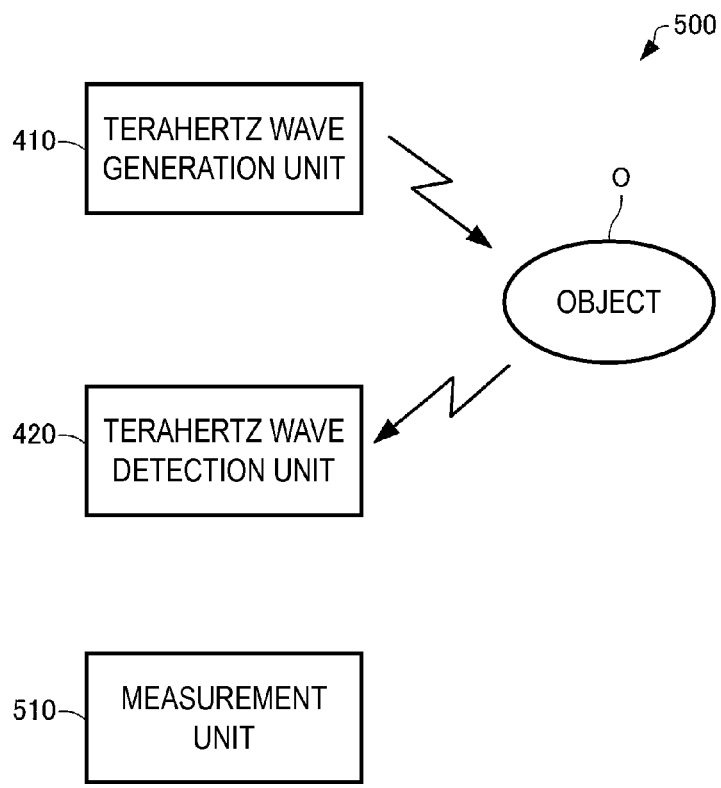
FIG. 28 is a block diagram schematically showing a measurement apparatus according to the fifth embodiment.

Next, a measurement apparatus 500 according to the fifth embodiment will be explained with reference to the drawings. FIG. 28 is a block diagram showing the measurement apparatus 500 according to the fifth embodiment.

As below, in the measurement apparatus 500 according to the fifth embodiment, the members having the same functions as those of the component members of the above described imaging apparatus 400 according to the fourth embodiment have the same signs and their detailed explanation will be omitted. This applies to a camera 600 according to the sixth embodiment to be described.

The measurement apparatus 500 includes a terahertz wave generation unit 410 that generates terahertz wave, a terahertz wave detection unit 420 that detects terahertz wave output from the terahertz wave generation unit 410 and transmitted through an object O or reflected by the object O, and a measurement unit 510 that measures the object O based on the detection result of the terahertz wave detection unit 420 as shown in FIG. 28.

Next, a usage example of the measurement apparatus 500 will be explained. When spectroscopic measurement of the object O is performed using the measurement apparatus 500, first, terahertz wave is generated by the terahertz wave generation unit 410, and the terahertz wave is applied to the object O. Then, the terahertz wave transmitted through the object O or reflected by the object O is detected by the terahertz wave detection unit 420. The detection result is sent out to the measurement unit 510. Note that the application of the terahertz wave to the object O and the detection of the terahertz wave transmitted through the object O or reflected by the object O are performed with respect to the entire object O.

In the measurement unit 510, the respective strengths of the terahertz waves that have passed through the first area 421, the second area 422, the third area 423, and the fourth area 424 forming each pixel 42 of the filter 40 are grasped from the detection result, and analyses of the components of the object O and their distributions or the like are performed.

According to the measurement apparatus 500, the photo conductive antenna 100 that can generate terahertz wave with the higher strength is provided. Accordingly, the measurement apparatus 500 may have the higher detection sensitivity.

6. Sixth Embodiment

Figure 29:
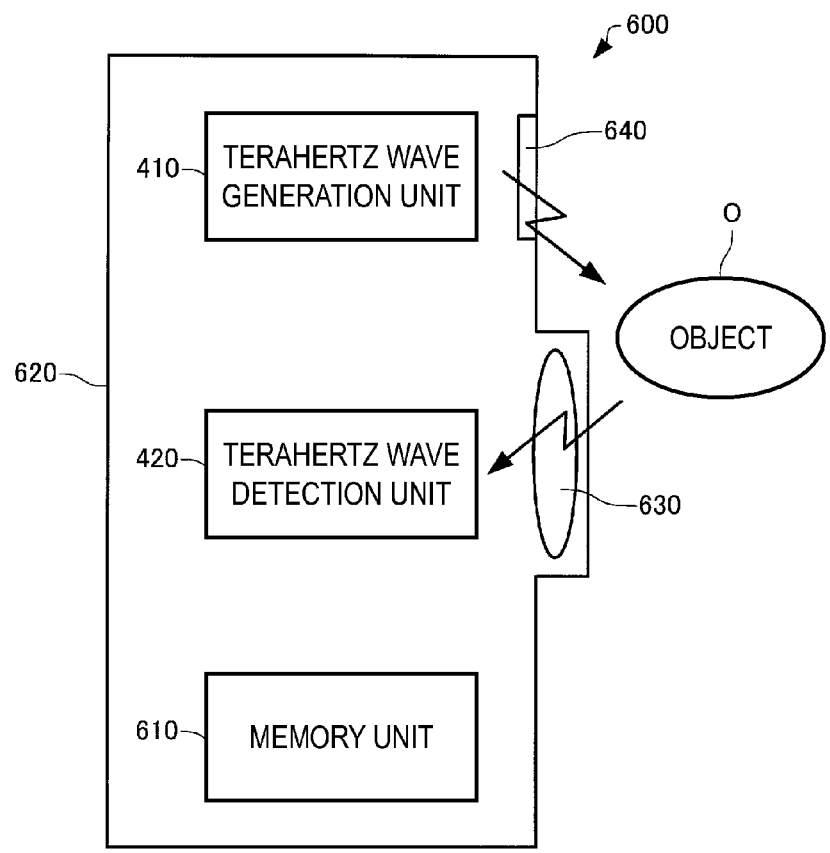
FIG. 29 is a block diagram schematically showing a camera according to the sixth embodiment.
Figure 30:
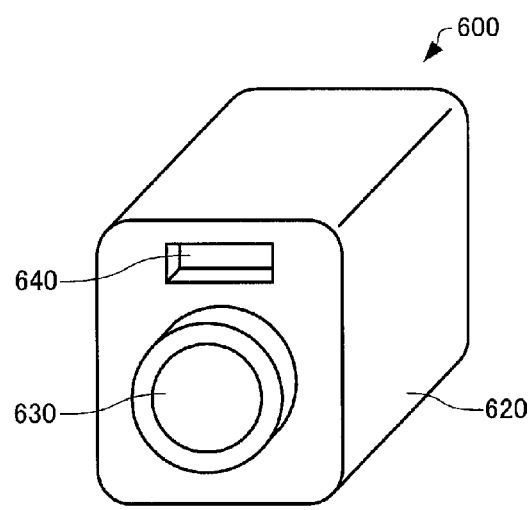
FIG. 30 is a perspective view schematically showing the camera according to the sixth embodiment.

Next, the camera 600 according to the sixth embodiment will be explained with reference to the drawings. FIG. 29 is a block diagram showing the camera 600 according to the sixth embodiment. FIG. 30 is a perspective view schematically showing the camera 600 according to the sixth embodiment.

The camera 600 includes a terahertz wave generation unit 410 that generates terahertz wave, a terahertz wave detection unit 420 that detects terahertz wave output from the terahertz wave generation unit 410 and transmitted through an object O or reflected by the object O, and a memory unit 610 that stores the detection result of the terahertz wave detection unit 420 as shown in FIGS. 29 and 30. Further, the respective units 410, 420, 610 are housed in a casing 620 of the camera 600. Furthermore, the camera 600 includes a lens (optical system) 630 that converges (images) the terahertz wave reflected by the object O on the terahertz wave detection unit 420, and a window part 640 for the terahertz wave generated in the terahertz wave generation unit 410 to exit to the outside of the casing 620. The lens 630 and the window part 640 include members of silicon, quartz, polyethylene, or the like that transmit and refract terahertz wave. Note that the window part 640 may have a configuration in which an opening is simply provided like a slit.

Next, a usage example of the camera 600 will be explained. When an object O is imaged by the camera 600, first, terahertz wave is generated by the terahertz wave generation unit 410, and the terahertz wave is applied to the object O. Then, the terahertz wave reflected by the object O is converged (imaged) on the terahertz wave detection unit 420 by the lens 630 and detected. The detection result is sent out to the memory unit 610 and stored. Note that the application of the terahertz wave to the object O and the detection of the terahertz wave reflected by the object O are performed with respect to the entire object O. Further, the detection result may be sent out to an external device such as a personal computer. In the personal computer, respective processing may be performed based on the detection result.

According to the camera 600, the photo conductive antenna 100 that can generate terahertz wave with the higher strength is provided. Accordingly, the camera 600 may have the higher detection sensitivity.

In addition, the terahertz wave generator including the photo conductive antenna according to the invention may be applied in medical fields and may contribute to various treatments and early detections. For example, the terahertz wave generator may contribute to improvements in accuracy of cancer screening and improvements in analysis accuracy of DNAs and proteins. Note that the photo conductive antenna according to the invention may be applied to a terahertz wave detector that detects terahertz wave.

The above described embodiments and modified examples are just examples and the invention is not limited to those. For example, the respective embodiments and the respective modified examples may be appropriately combined.

The invention includes substantially the same configurations (for example, the configurations having the same functions, methods, and results, or the configurations having the same purposes and effects) as the configurations explained in the embodiments. Further, the invention includes the configurations in which non-essential parts of the configurations explained in the embodiments are replaced. Furthermore, the invention includes the configurations that may exert the same effects or the configurations that may achieve the same purposes as those of the configurations explained in the embodiments. In addition, the invention includes the configurations in which known technologies are added to the configurations explained in the embodiments.

The entire disclosure of Japanese Patent Application No. 2013-036770, filed Feb. 27, 2013 is expressly incorporated by reference herein.

What is claimed is:

1. A photo conductive antenna irradiated with light pulse and generating terahertz wave, comprising:
   a first layer formed by a semi-insulating substrate;
   a second layer located on the first layer and formed using a material having lower carrier mobility than carrier mobility of the semi-insulating substrate;
   a first electrode and a second electrode located on the second layer and applying a voltage to the first layer;
   a first region in which the second layer is formed on the first layer; and
   a second region in which the second layer is not formed on the first layer,
   wherein the second region is located between the first electrode and the second electrode in a plan view from a stacking direction of the first layer and the second layer, and
   the second region is configured to have a light pulse applied thereto.

2. The photo conductive antenna according to claim 1, wherein the first electrode has a first projecting part that projects from the first electrode toward the second electrode side in the plan view,
   the second electrode has a second projecting part that projects from the second electrode toward the first electrode side in the plan view, and
   the first region and the second region are provided in a region between the first projecting part and the second projecting part in the plan view.

3. The photo conductive antenna according to claim 2, wherein the first electrode and the second electrode apply a direct-current voltage to the first layer,
   the first electrode is a positive electrode,
   the second electrode is a negative electrode, and
   a distance between an edge of the second region nearest to the first projecting part and the first projecting part is larger than a distance between an edge of the second region and the second projecting part and the second projecting part in the plan view.

4. A terahertz wave generator comprising:
   a light pulse generation unit configured to generate the light pulse; and
   the photo conductive antenna according to claim 3.

5. A camera comprising:
   a light pulse generation unit configured to generate the light pulse;
   the photo conductive antenna irradiated according to claim 3;
   a terahertz wave detection unit configured to detect the terahertz wave output from the photo conductive antenna and transmit the terahertz wave through an object or reflected by the object; and
   a memory unit configured to store a detection result of the terahertz wave detection unit.

6. An imaging apparatus comprising:
   a light pulse generation unit configured to generate the light pulse;
   the photo conductive antenna according to claim 3;
   a terahertz wave detection unit configured to detect the terahertz wave output from the photo conductive antenna and transmit the terahertz wave through an object or reflected by the object; and
   an image formation unit configured to generate an image of the object based on a detection result of the terahertz wave detection unit.

7. A measurement apparatus comprising:
   a light pulse generation unit configured to generate the light pulse;
   the photo conductive antenna according to claim 3;
   a terahertz wave detection unit configured to detect the terahertz wave output from the photo conductive antenna and transmit the terahertz wave through an object or reflected by the object; and
   a measurement unit configured to measure the object based on a detection result of the terahertz wave detection unit.

8. The photo conductive antenna according to claim 2, wherein the first electrode and the second electrode are configured to apply an alternating-current voltage to the first layer, and
   a distance between an edge of the second region nearest to the first projecting part and the first projecting part is larger than a distance between an edge of the second region and the second projecting part and the second projecting part in the plan view.

9. A terahertz wave generator comprising:
   a light pulse generation unit configured to generate the light pulse; and
   the photo conductive antenna according to claim 2.

10. A camera comprising:
    a light pulse generation unit configured to generate the light pulse;
    the photo conductive antenna according to claim 2;
    a terahertz wave detection unit configured to detect the terahertz wave output from the photo conductive antenna and transmit the terahertz wave through an object or reflected by the object; and
    a memory unit configured to store a detection result of the terahertz wave detection unit.

11. An imaging apparatus comprising:
a light pulse generation unit configured to generate the light pulse;
the photo conductive antenna according to claim 2;
a terahertz wave detection unit configured to detect the terahertz wave output from the photo conductive antenna and transmit the terahertz wave through an object or reflected by the object; and
an image formation unit configured to generate an image of the object based on a detection result of the terahertz wave detection unit.

12. A measurement apparatus comprising:
a light pulse generation unit configured to generate the light pulse;
the photo conductive antenna according to claim 2;
a terahertz wave detection unit configured to detect the terahertz wave output from the photo conductive antenna and transmit the terahertz wave through an object or reflected by the object; and
a measurement unit configured to measure the object based on a detection result of the terahertz wave detection unit.

13. The photo conductive antenna according to claim 1, wherein the first electrode has a first projecting part that projects from the first electrode toward the second electrode side in the plan view,
the second electrode has a second projecting part that projects from the second electrode toward the first electrode side in the plan view, and
a region between the first projecting part and the second projecting part in the plan view is the second region.

14. The photo conductive antenna according to claim 1, further comprising a covering layer provided on a surface of the first layer.

15. The photo conductive antenna according to claim 1, wherein a recessed part is formed on a surface of the second layer, and
the first electrode and the second electrode are provided in the recessed part.

16. A terahertz wave generator comprising:
a light pulse generation unit configured to generate the light pulse; and
the photo conductive antenna according to claim 1.

17. A camera comprising:
a light pulse generation unit configured to generate the light pulse;
the photo conductive antenna according to claim 1;
a terahertz wave detection unit configured to detect the terahertz wave output from the photo conductive antenna and transmit the terahertz wave through an object or reflected by the object; and
a memory unit configured to store a detection result of the terahertz wave detection unit.

18. An imaging apparatus comprising:
a light pulse generation unit configured to generate the light pulse;
the photo conductive antenna according to claim 1;
a terahertz wave detection unit configured to detect the terahertz wave output from the photo conductive antenna and transmit the terahertz wave through an object or reflected by the object; and
an image formation unit configured to generate an image of the object based on a detection result of the terahertz wave detection unit.

19. A measurement apparatus comprising:
a light pulse generation unit configured to generate the light pulse;
the photo conductive antenna according to claim 1;
a terahertz wave detection unit configured to detect the terahertz wave output from the photo conductive antenna and transmit the terahertz wave through an object or reflected by the object; and
a measurement unit configured to measure the object based on a detection result of the terahertz wave detection unit.

* * * * *